(12) United States Patent  (10) Patent No.: US 7,397,058 B2
Struble et al.  (45) Date of Patent: Jul. 8, 2008

(54) SYSTEM FOR CONTROLLING IMAGE QUALITY IN PROCESSING RADIOGRAPHIC PHOTOTHERMOGRAPHIC SHEET MEDIA

(75) Inventors: Kent R. Struble, Woodbury, MN (US); Graham F. Nelson, Saint Paul, MN (US); Duane S. Olmsted, Eagan, MN (US)

(73) Assignee: Carestream Health, Inc., Rochester, NY (US)

( * ) Notice: Subject to any disclaimer, the term of this patent is extended or adjusted under 35 U.S.C. 154(b) by 224 days.

(21) Appl. No.: 11/074,102

(22) Filed: Mar. 7, 2005

(65)  Prior Publication Data

US 2006/0197994 A1  Sep. 7, 2006

(51) Int. Cl.
  *G01T 1/11*  (2006.01)
(52) U.S. Cl. ...................................... 250/584
(58) Field of Classification Search ................... 250/584
  See application file for complete search history.

(56)  References Cited

U.S. PATENT DOCUMENTS

| | | |
|---|---|---|
| 5,229,585 A | 7/1993 | Lemberger et al. |
| 5,473,400 A | 12/1995 | Lemberger et al. |
| 5,481,657 A | 1/1996 | Schubert et al. |
| 5,572,285 A | 11/1996 | Takagai |
| 5,757,021 A | 5/1998 | Dewaele |
| 6,007,971 A | 12/1999 | Star et al. |
| 6,020,909 A | 2/2000 | Kocher et al. |
| 6,023,285 A | 2/2000 | Kocher et al. |
| 6,223,585 B1 | 5/2001 | Krogstad |
| 6,520,694 B1* | 2/2003 | Hall et al. .................... 396/567 |
| 6,710,891 B1* | 3/2004 | Vraa et al. ................. 358/1.12 |
| 6,811,079 B1* | 11/2004 | Vraa et al. ................... 235/383 |
| 6,945,713 B2* | 9/2005 | Vraa et al. ................... 396/511 |
| 2003/0142858 A1* | 7/2003 | Motoki ....................... 382/132 |
| 2004/0156063 A1* | 8/2004 | Vraa et al. ................. 358/1.12 |
| 2004/0184801 A1* | 9/2004 | Vraa et al. ................... 396/517 |

FOREIGN PATENT DOCUMENTS

| EP | 1 189 106 | 3/2002 |
|---|---|---|
| EP | 1189106 A2 * | 3/2002 |

* cited by examiner

*Primary Examiner*—David P. Porta
*Assistant Examiner*—David S Baker

(57)  ABSTRACT

A method and system for controlling image quality in processing radiographic photothermographic sheet media. A cassette removably contains radiographic photothermographic sheet media and also has an information member. The information member stores information including size of the sheet media stored in the cassette and calibrated conditions for processing the sheet media. A thermal media processor processes an exposed sheet media in accordance with the calibrated processing conditions.

4 Claims, 24 Drawing Sheets

US 7,397,058 B2

SYSTEM FOR CONTROLLING IMAGE QUALITY IN PROCESSING RADIOGRAPHIC PHOTOTHERMOGRAPHIC SHEET MEDIA

FIELD OF THE INVENTION

This invention relates in general to sheet media imaging systems and more particularly to a system for controlling image quality in processing radiographic photothermographic sheet media.

BACKGROUND OF THE INVENTION

Sheet media imaging systems include radiographic imaging systems which produce radiographic images on photosensitive sheet media such as film or paper. The photosensitive media is typically contained in a light tight cassette to facilitate handling and to shield the photosensitive media from exposure to external light. In film-screen analog radiography, the cassette includes one or two fluorescent screens which sandwich the photosensitive film in the openable, cassette. The cassette is positioned in back of the body part of a patient to be x-rayed. An x-ray source projects x-rays through the body part to irradiate the fluorescent screen(s) which emit a light image to produce a latent radiographic image of the body part in the photosensitive media. The media is then processed to produce in the media a visual radiographic image of the body part for observation and diagnosis.

Health imaging professionals require that diagnostic radiographic images be controlled within a narrow range of contrast and density to be acceptable. Because analog imaging uses direct x-ray exposures through a patient, retaking an image to get a correct exposure is undesirable, since it is expensive and time consuming and since it would expose the patient to more x-radiation. Where the radiographic sheet media is chemically processable, there is greater consistency in both the manufacture of the sheet media as well as the processing conditions of the media. Dry photothermographic media tends to be more variable in its manufacture and also tends to be more sensitive to the environment in which it is stored prior to use. These factors mean that the media density and contrast may vary unacceptably for the user. Laser imaged media can control its output simply by adjusting the intensity of the laser. In contrast, analog media is exposed from a variety of x-ray sources that cannot be easily controlled in an automated fashion. Thus, the image quality of dry photothermographic film may vary unacceptably unless a solution is found to reduce that variability. Sources of variability include manufacturing variability, media storage conditions such as humidity and temperature, age of the media, and ambient conditions at the time of processing the media.

The key to a successful processing system for heat processable photothermographic media is to ensure consistent output quality of the media, while not imposing additional workload on the users of the system. Adjusting the processing cycle allows the density and contrast of the media to be adjusted. One problem is determining what processing cycle to give each sheet of media. Since the sheets of media presented to the processor system may have multiple sizes, may come from multiple manufacturing lots, may be of different ages and have seen different storage conditions, each media sheet may need a different processing cycle.

Sheet media imaging systems also include laser imaging systems which produce medical images on photosensitive sheet film from digital medical images generated by diagnostic imaging systems (MRI, CT, US, PET), computed radiography (CR) systems, medical image digitizers, digital or analog medical image archives, direct digital radiography or the like. The sheet film can be packaged in optically opaque packaging which is removed under dark room conditions and loaded into a film supply of a laser imager. Dark room film loading is eliminated by the resealable film cartridge disclosed in U.S. Pat. No. 5,473,400 (Lemberger). The disclosed cartridge allows for daylight loading and can be reused and removed from the laser imager. U.S. Pat. No. 5,229,585 (Lemberger) discloses a bar code system which uses this resealable cartridge to control a laser imaging system. The cartridge has attached to it an optical bar code with a unique cartridge ID, film size, film type information and film sensitometric information. The laser imager has a bar code scanner which reads information from the bar code as the cartridge is opened. An imager management system controls the laser imager as a function of the input data and the information read from the bar code. A film processor develops the film as a function of film type information read from the bar code. The laser imager stores information relating to film usage of the cartridge.

U.S. Pat. No. 5,481,657, issued Jan. 2, 1996 (inventors Schubert et al.), discloses a multi-user digital laser imaging system wherein a calibration process is used including laser exposing a calibration film to a range of density patches, processing the film, measuring the density patches with a densitometer, comparing the measured densities with expected density values of a stored film model for the film, and modifying the film model if any discrepancies are noted.

U.S. Pat. No. 6,710,891 B1, issued Mar. 23, 2004, inventors Vraa et al., discloses a sheet media imaging system including a laser imager configured to operate with a resealable media cartridge having an RFID transponder storing relevant digital data that communicates with a laser imager transceiver.

U.S. Pat. No. 6,023,285, issued Feb. 8, 2000, inventors Kocher et al., discloses a photothermographic laser imaging system including a laser printer for exposing photothermographic media to digital data, a thermal processor for thermally developing the exposed photothermnographic media to render a visual image of the digital data and a densitometer for reading the density of the visual image. A method for establishing calibration of the system includes reading optimum thermal processing parameters including processor temperature from a bar code associated with unexposed photothermographic media; setting the thermal processor to operate at the read parameters; exposing a multiple step gray scale pattern calibration media by the laser printer; reading with the densitometer the densities of the multiple step gray scale pattern from the developed calibration media; and adjusting the temperature of the thermal processor if the measured densities are not within desired limits. (See also: U.S. Pat. No. 6,020,909, issued Feb. 1, 2000, inventors Kocher et al., and U.S. No. Pat. 6,223,585 B1, issued May 1, 2001, inventor Krogstad.)

U.S. Pat. No. 5,757,021, issued May 26, 1998, inventor Dewaele, is of interest in disclosing an identification system for use in the field of digital radiography including a cassette carrying a photostimulable phosphor screen which has an RF tag provided on the cassette. Patient identification data and examination type are stored in the RF tag by a health care provider and after the screen is exposed to an x-ray image, the RF tag and phosphor screen are read out and the radiation image is digitally processed in accordance with image processing parameters associated with the examination type and stored in the readout device. The RF tag is then erased.

Although the foregoing patents disclose systems that may have been useful for the purposes for which they were intended, none of them solve the problems discussed above relating to controlling image quality in processing x-ray exposed radiographic media, especially heat processable photothermographic media.

There is thus a need in a sheet media imaging system for a system for controlling image quality in processing x-ray exposed radiographic media, especially heat processable photothermographic film, which ensures consistent quality output of the media, while imposing minimal workload on the users of the system.

SUMMARY OF THE INVENTION

According to the present invention, there is provided a solution to the needs discussed above.

According to a feature of the present invention, there is provided a method of controlling image quality in processing radiographic photothermographic sheet media, comprising the steps of: providing a cassette for removably containing radiographic photothermographic sheet media, said cassette having an information member; and storing in said information member information including size of said sheet media stored in said cassette and calibrated conditions for processing said sheet media.

According to another feature of the present invention, there is provided a system for controlling image quality in processing radiographic photothermographic sheet media, comprising: a cassette for removably containing radiographic photothermographic sheet media; and an information member associated with said cassette for storing information including size of sheet media contained in said cassette and calibrated conditions for processing said sheet media contained in said cassette.

According to still another feature of the present invention there is provided a method for controlling image quality in processing radiographic photothermographic sheet media, comprising the steps of: providing a media processor for processing radiographic photothermographic sheet media, said media processor having a digital data memory and control system for storing digital data relating to processing conditions for at least one size of sheet media and for controlling said media processor; providing packaging of unexposed radiographic photothermographic sheet media of said at least one size, said packaging having an information member storing relevant digital data including sheet media size and manufacturer's originated media processing conditions; replacing any media processing conditions for said at least one size of sheet media stored in said processor digital data memory and control system with the manufacturer's originated media processing conditions stored on said packaging information member; providing a calibration sheet media from said packaging of unexposed sheet media, said calibration sheet media having a plurality of different density regions; processing said calibration sheet media by means of said media processor in accordance with the manufacturer's originated media processing conditions; measuring the plurality of density regions of said processed calibration sheet media; and modifying said stored manufacturer's originated processing conditions for said at least one size of sheet media as a function of variations in measured calibration densities to expected densities, so as to store in said processor digital data memory and control system calibrated media processing conditions for use in processing subsequent sheet media from said packaging.

The present invention provides several advantages. For example, the image quality of radiographic photothermographic sheet media is controlled during processing in a simple and efficient manner. In addition, the processing of radiographic photothermographic sheet media is carried out to ensure consistent quality output of the media while imposing minimal workload on the users of the system.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
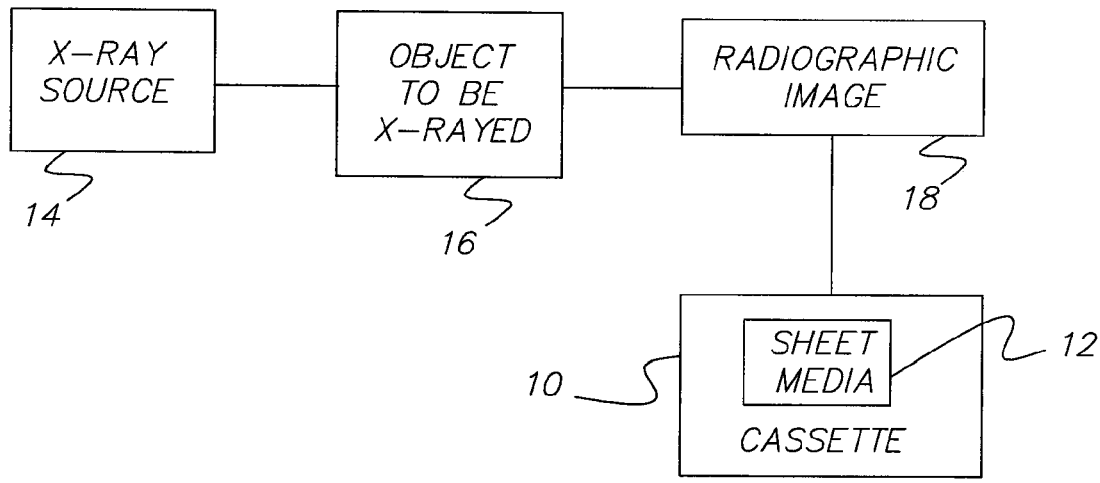
FIG. 1 is a block diagram of a procedure for producing a radiographic image in radiographic sheet media contained in a cassette.

The following is a detailed description of the preferred embodiments of the invention, reference being made to the drawings in which the same reference numerals identify the same elements of structure in each of the several figures.

According to the present invention, there is provided system and method for controlling image quality in the processing of heat processable photothermographic sheet media which has been exposed to x-radiation. Broadly, the invention includes, determining the appropriate processing cycle for an exposed sheet media, communicating the appropriate processing cycle to a sheet media processor, and processing the sheet media according to the appropriate processing cycle, making any changes to the processor processing condition as needed. The appropriate processing cycle for sheet media can be determined using either an open loop approach or the preferred closed loop calibration approach to be described in greater detail later. The processing conditions that can be adjusted using a closed loop calibration approach include varying processing temperature(s) of the media processor and/or varying dwell time by changing media transport speed (dwell time) through the processor. The latter adjustment is more practical due to the time required to change temperature.

Referring now to FIG. 1, there is shown a typical procedure for exposing a radiographic sheet media. As shown, radiographic sheet media 12 is removably contained in a cassette 10. An x-ray source 14 projects x-rays through an object 16 to be x-rayed (such as a patient's body part) to produce a radiographic image 18 which is stored as a latent radiographic image in radiographic sheet media 12 contained in cassette 10. The radiographic sheet media 12 is preferably heat processable photothermographic media.

Figure 2:
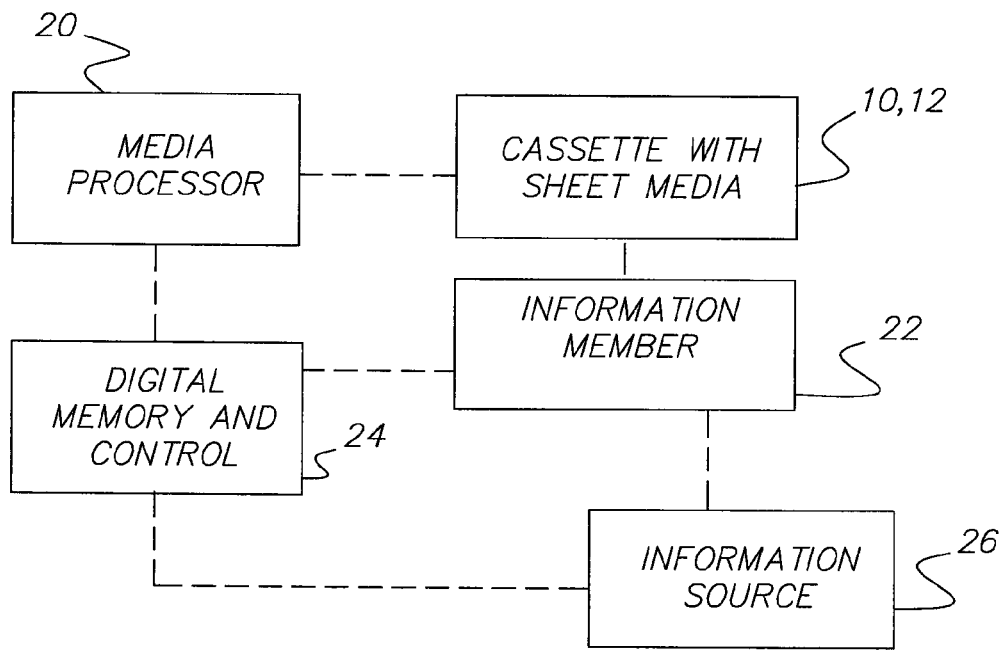
FIG. 2 is a block diagram of an embodiment of the present invention.

As shown in FIG. 2, the exposed sheet media 12 is removed from cassette 10 and is processed in media processor 20. In the case of photothermographic media, media processor 20 constitutes a heat processor which develops exposed sheet media 12 by applying heat to media 12 for a desired time period. Due to the variability in manufacture of photothermographic media and the sensitivity of such media to environmental conditions such as media age and storage temperature and humidity, according to the present invention, image quality during processing is improved by storing calibrated processing conditions in an information member 22 associated with cassette 10. The calibrated processing conditions are communicated to digital memory and control 24 of processor 20. Control 24 stores the calibrated processing conditions and controls the processing of media 12 as a function of such calibrated processing conditions. The calibrated processing conditions are communicated to information member 22 by information source 26 which may or may not be part of control 24.

Figure 3:
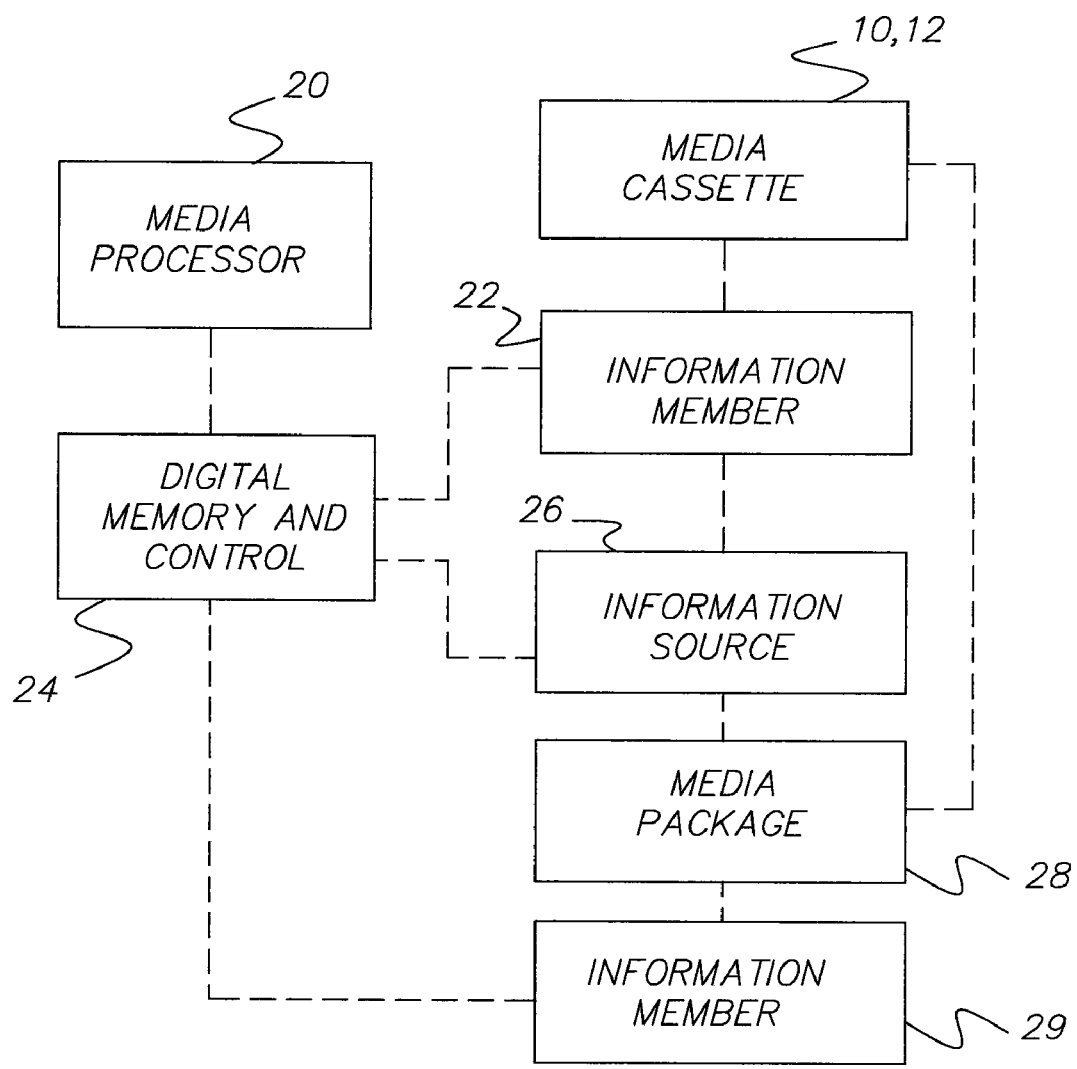
FIG. 3 is a block diagram of another embodiment of the present invention.

As shown in FIG. 3, according to another feature of the present invention, media package 28 contains a stack of unexposed sheet media 12. A media sheet 12 is placed in cassette 10, exposed to a radiographic image and subsequently received by processor 20 which processes media 12. Media package 28 has an associated information member 29 which stores digital data relating to media 12, such as media size, date of manufacture, media speed, package ID number and manufacturer's originated media processing conditions. This digital data is communicated to control 24 of processor 20 where it is used to determine the calibrated processing conditions for processing subsequent sheet media 12 from package 28. The calibrated processing conditions are communicated by control 24 to information member 22 of cassette 10.

Figure 4:
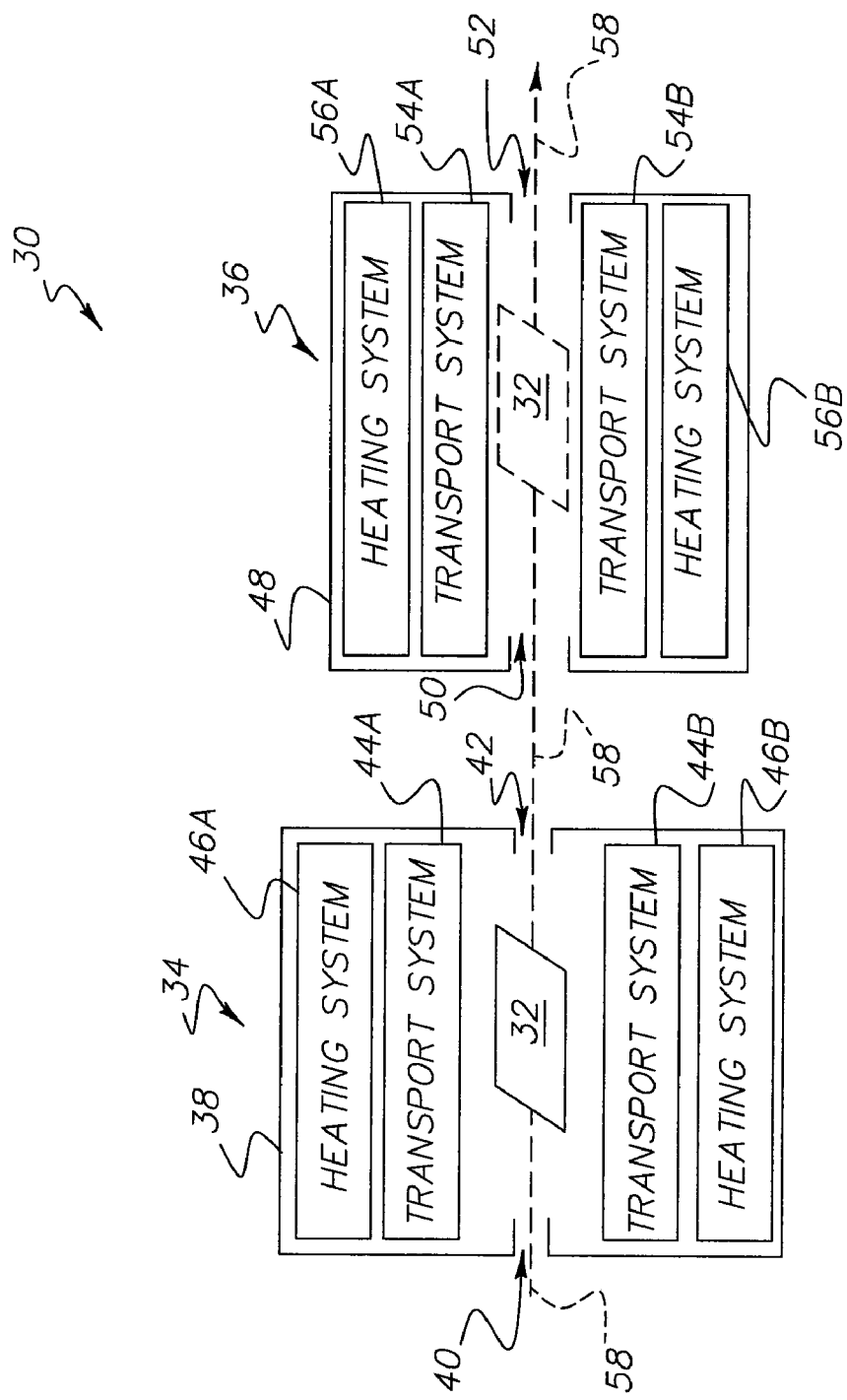
FIG. 4 is a block diagram of an exemplary sheet media thermal processor that can be used in carrying out the present invention.

FIG. 4 is a block diagram illustrating a thermal processor 30 for developing an image in an imaging material (media) 32 having a conditioning threshold temperature and a development threshold temperature.

One type of gelatin-based photothermographic imaging material suitable for development by thermal processor 30 comprises a base material coated on each side with an aqueous-based emulsion of heat sensitive materials, including developers, in an aqueous-based solvent. When heated to a temperature at or above a conditioning threshold temperature, fluid, consisting primarily of water, is released in vaporous form from the emulsion, leaving the heat sensitive materials on the imaging material. When subsequently heated to a temperature at or above a development threshold temperature, the heat sensitive materials react to form an image on the imaging material.

Thermal processor 30 includes a preheat chamber 34 and a dwell chamber 36 that is thermally isolated from preheat chamber 34. Preheat chamber 34 includes a housing 38, having an entrance 40 and an exit 42, enclosing a transport system 44 (including upper system 44a and lower system 44b) and a heating system 46 (including upper system 46a and lower system 46b). Dwell chamber 36 includes a housing 48, having an entrance 50 and an exit 52, enclosing a transport system 54 (including upper system 54a and lower system 54b) and a heating system 56 (including upper system 56a and lower system 56b).

Preheat chamber 34 receives imaging material 32 at an ambient temperature and with the emulsion having an arbitrary moisture level at entrance 40. Transport system 44 moves imaging material 32 through preheat chamber 34 along a transport path 58 from entrance 40 to exit 42. As imaging material 32 moves through preheat chamber 34, heating system 46 heats imaging material 32 to a desired conditioning temperature at least equal to the imaging material's preconditioning threshold temperature but less than the development threshold temperature. The desired conditioning temperature is preferably within a conditioning temperature range. Preheat chamber 34 maintains the imaging material at the conditioning temperature for a conditioning period at least long enough for substantially all of the water/moisture to be released from the emulsion.

Transport system 44 receives imaging material 32 at the ambient temperature at entrance 40, moves imaging material 32 along transport path 58, and provides imaging material 32 at exit 42 at substantially the conditioning temperature and with substantially all of the water/moisture released from the emulsion. Dwell chamber 36 receives imaging material 32 from preheat chamber 34 at entrance 50, with imaging material 32 at a temperature substantially equal to the conditioning temperature and with substantially all of the water/moisture released from the emulsion. Transport system 54 moves imaging material 32 through dwell chamber 36 along transport path 58 in proximity to heating system 56 from entrance 50 to exit 52.

As imaging material 32 is transported through dwell chamber 36, heating system 56 heats imaging material 32 from the preconditioning temperature to a development temperature at least equal to the development threshold temperature. Dwell chamber 36 maintains imaging material 32 at the development temperature for a development period that will provide substantially optimal development of the image in imaging material 32. Transport system 54 moves imaging material 32 through dwell chamber 36 at a rate such that imaging material 32 is maintained at the desired development temperature for a development period.

By substantially removing all of the moisture from the aqueous-based emulsion of imaging material 32 at preheat chamber 34 prior to providing imaging material 32 to dwell chamber 36 for development, thermal processor 30 minimizes the potential of visual artifacts due to excessive moisture levels and minimizes the potential for variations in image quality from film to film. Furthermore, by heating imaging material 32 to the conditioning temperature prior to its entering dwell chamber 36, dwell chamber 36 needs to raise the temperature of imaging material 32 to the developing temperature from the conditioning temperature rather than the ambient temperature, thereby reducing visual artifacts caused by expansion of the base material.

Figure 5:
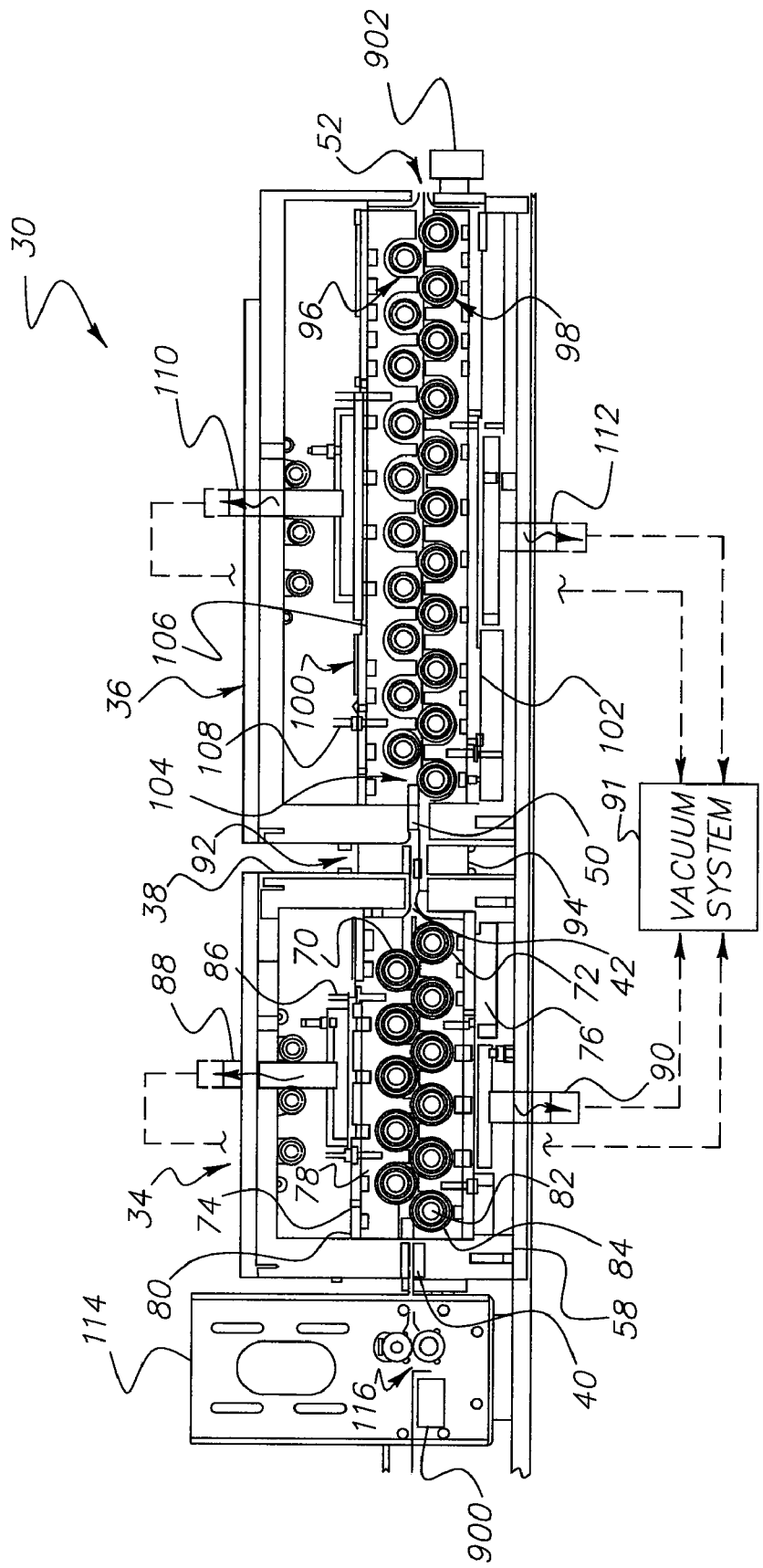
FIG. 5 is an elevational side view of a more detailed rendering of the thermal processor shown in FIG. 4.

FIG. 5 is a cross-sectional view illustrating a flat bed thermal processor 30, including preheat chamber 34 and dwell chamber 36. Transport system 44 includes a plurality of upper rollers 70 and a plurality of lower rollers 72. Heating system 46 includes an upper heating member 74 and a lower heating member 76, with each heating member including a heat plate 78 and a corresponding heat blanket 80.

Rollers 70 and 72 can include support shafts 82 having cylindrical sleeves of support material 84 surrounding the external surface of shafts 72. Support shafts 82 are rotatably mounted to opposite sides of enclosure 38 in a spaced relationship along transport path 58 between entrance 40 and exit 42, such that support material 84 contacts imaging material 32.

One or more of the rollers 70, 72 can be driven in order to drive imaging material 32 through preheat chamber 34 adjacent to the heating plates of heating members 74, 76 along transport path 58. In one preferred embodiment, all of the rollers 70, 72 are driven so that the surface of each roller is heated uniformly when no imaging material is contacting rollers 70, 72. Rollers 70, 72 are driven at a rotational speed such that imaging material 32 is maintained at a desired conditioning temperature for a desired conditioning period before exiting preheat chamber 34 at exit 42.

As illustrated, upper roller 70 can be positioned relative to lower rollers 72 to cause imaging material 32 to be bent or curved in an undulating fashion when transported between rollers 70, 72. Creating these curvatures can be accomplished, as shown, by horizontally offsetting upper rollers 70 from lower rollers 72 and vertically positioning them such that the upper rollers 70 and lower rollers 72 overlap a horizontal transport path 58. Curving imaging material 32 in this fashion increases a column stiffness of imaging material 32 and enables imaging material 32 to be transported through and heated to a conditioning temperature within preheat chamber 34 without a need for nip rollers or other pressure transporting means. Consequently, thermally-induced wrinkles of imaging material 32 associated with "nipping" or pressure can be minimized.

Upper rollers 70 can be sufficiently spaced apart, as can lower rollers 72, so that imaging material 32 can expand with minimal constraint in the direction generally perpendicular to transport path 58. This minimizes the potential for formation of significant wrinkles across imaging material, generally perpendicular to the direction of transport path 58. Furthermore, the minimization of these wrinkles can be accomplished without requiring that imaging material 32 be under tension when transported through preheat chamber 34. This is particularly important when developing imaging material 32 of relatively short lengths.

Heating system 46 includes an upper heating member 74 and a lower heating member 76. Heating members 74, 76 each include a heat plate 78 and, as illustrated, can be heated with a corresponding heat blanket 80. In one embodiment, heat plates 78 can be aluminum. Heat plates 78 associated with heating members 74, 76 can be configured with multiple zones with the temperature of each zone individually controlled, for example, by a controller (not shown) and a temperature sensor 86 corresponding to each zone, such as a resistance temperature device or a thermocouple.

Likewise, heat blankets 80 can be configured with multiple zones, with each zone corresponding to one of the heat plate zones and providing a temperature based on temperature sensor 86 of the corresponding heat plate zone. As illustrated, heat plates 78 are shaped to partially wrap around a portion of the circumference of rollers 70, 72. By partially nesting rollers 70, 72 within heat plates 78 in this fashion, heating members 74 and 76 can more effectively maintain the temperature of the outer surfaces of rollers 70, 72, resulting in their providing a more uniform heat transfer to imaging material 32. By positioning heating members 74, 76 proximate to each side of transport path 58, each side of imaging material 32 is heated as it passes through preheat chamber 34.

Preheat chamber 34 includes an evacuation system that includes exhaust ports 88 and 90 that are configured to couple to an external vacuum system 91. External vacuum system 91 is configured to draw air from preheat chamber 34 to thereby exhaust air and substantially all water vapor and other byproducts released from the aqueous-based emulsion of imaging material 32 from preheat chamber 34. The exhaust air is filtered after removal from preheat chamber 34. The evacuation system is configured such that external vacuum system 91 draws external air into preheat chamber 34 via entrance 40 and exit 42. Entrance 40 and exit 42 can be flow restricted or sealed, and the evacuation system configured to include passages or channels through heat plates 78 through which external vacuum system 91 draws external air so that the external air is heated prior to entering preheat chamber 34 to thereby better maintain the temperature of imaging material 32 at a desired conditioning temperature.

Thermal processor 30 includes a transition section 92 positioned between preheat chamber 34 and dwell chamber 36. Transition section 92 includes a guide channel 94 configured to guide imaging material 32 from exit 42 of preheat chamber 34 to entrance 50 of dwell chamber 36. In one embodiment, exit 42 of preheat chamber 34 and entrance 50 to dwell chamber 36 include seals to substantially maintain thermal isolation between preheat chamber 34 and dwell chamber 36.

As illustrated, dwell chamber 36 can be configured in a fashion similar to preheat chamber 34, with transport system 54 including a plurality of upper rollers 96 and a plurality of lower rollers 98. Likewise, heating system 56 includes an upper heating member 100 and a lower heating member 102, with each heating member including a heat plate 104 and a corresponding heating blanket 106. One or more of the rollers 96, 98 can be driven so as to move imaging material 32 through dwell chamber 36 along transport path 58 adjacent to heating members 100, 102. Rollers 100, 102 are driven at a rotational speed such that imaging material 32 is heated from the conditioning temperature to the developing temperature and held at the developing temperature for a desired developing period as it is transported through dwell chamber 36 from entrance 50 to exit 52.

Dwell chamber 36 includes an evacuation system that includes exhaust ports 110 and 112 that are configured to couple to external vacuum system 91. External vacuum system is configured to draw air from dwell chamber 36 through exhaust ports 110 and 112 in order to exhaust gaseous byproducts released by imaging material 32 during development.

Thermal processor 30 includes a receiver section 114. Receiver section 114 includes a pair of nip rollers 116 configured to receive imaging material 32 at an ambient temperature and to feed imaging material to transport system 44 of preheat chamber 34 via entrance 40. An exposure device 900 is provided in receiver section 114 to expose a calibration imaging material (sheet media) 32 to a plurality of different densities (step wedge). Exemplary exposure devices include an integrating cavity, an integrating sphere, and an LED/lenslet array. Near the exit 52 of processor 30 is a densitometer 902 for reading the densities of the calibration media density step wedge. Exposure device 900 and densitometer 902 can also be used to respectively expose sheet media to a density patch and to read the density patch in order to further control processing conditions.

Figure 6:
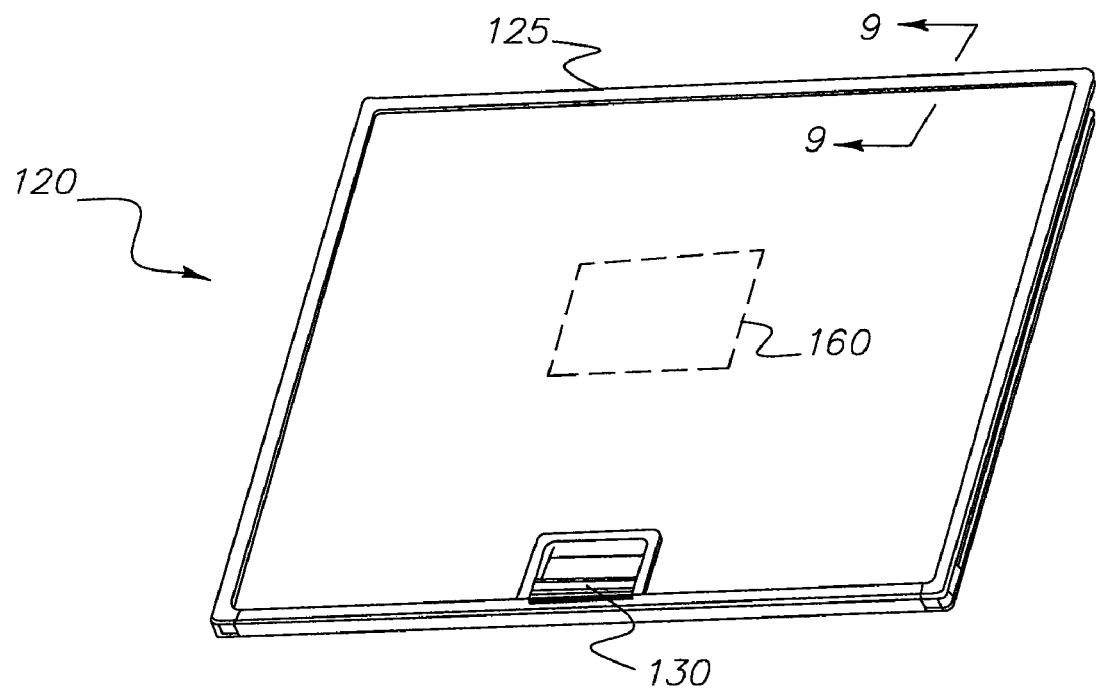
FIGS. 6-8 are perspective views of a sheet media cassette that can be used in carrying out the present invention, the cassette shown closed, partially open, and fully opened, respectively.
Figure 7:
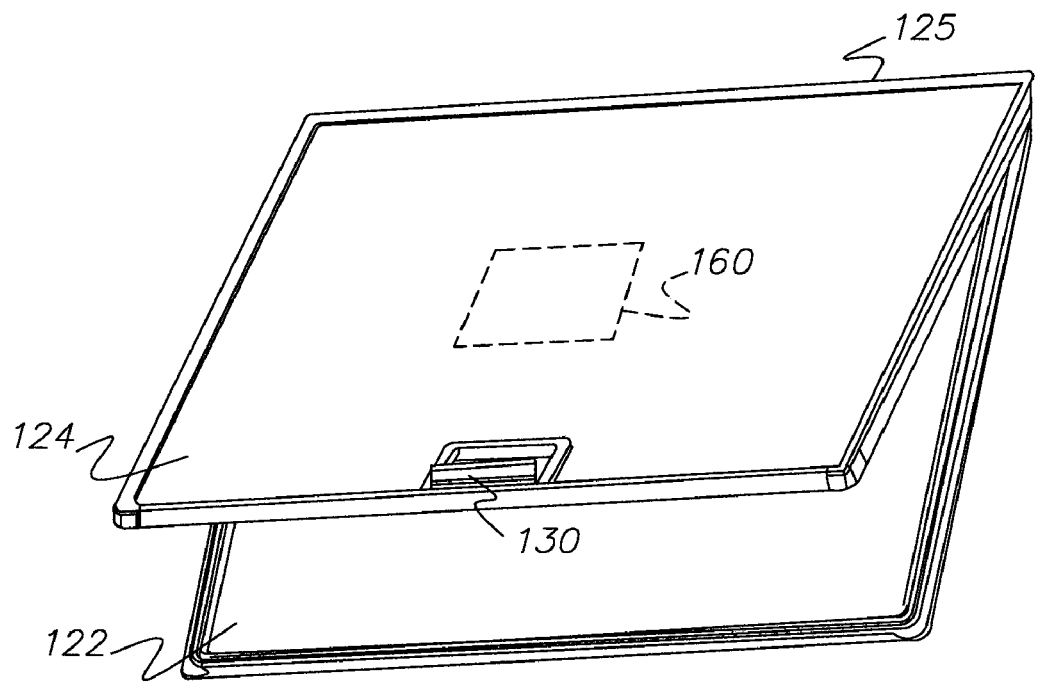
Figure 8:
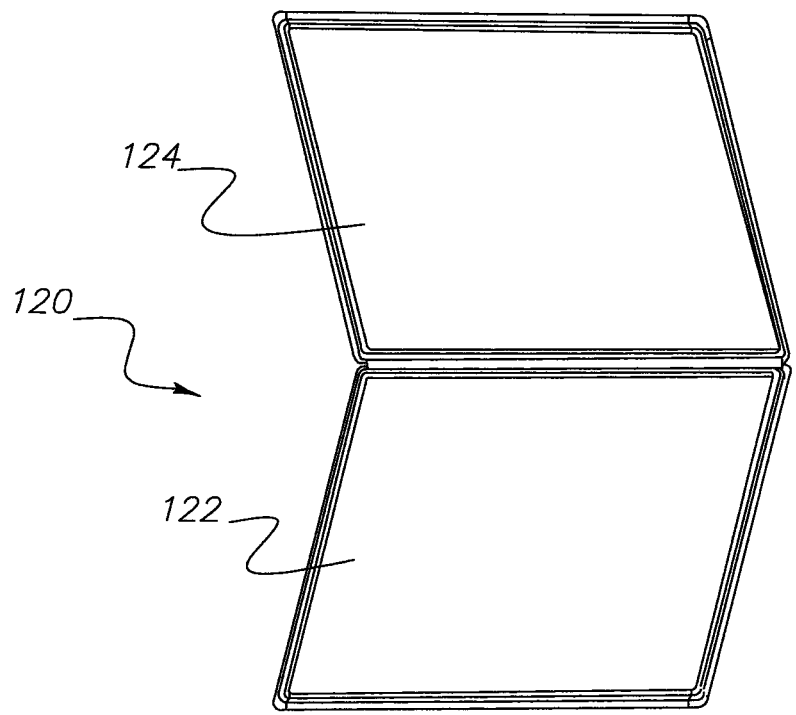

Referring now to FIGS. 6-9 there is shown an exemplary radiographic media cassette that can be used in implementing the present invention. FIG. 6 shows cassette 120 in a closed position and FIG. 7 shows cassette 120 in a partially opened position. Cassette 120 includes panels 122 and 124 hinged together by border 126. As described in greater detail in U.S. Pat. No. 5,912,944, panels 122 and 124 can be formed from a composite of aluminum, polypropylene, and aluminum material, and border 126 is formed from a thermoplastic elastomer which provides excellent light integrity, as well as shock resistance, and acts as a hinge to enable opening and closing of cassette 120. FIG. 8 shows cassette 120 in an opened position to facilitate insertion and removal of radiographic sheet media 135. The opening and closing of cassette 120 is facilitated by latch 130.

Figure 9:
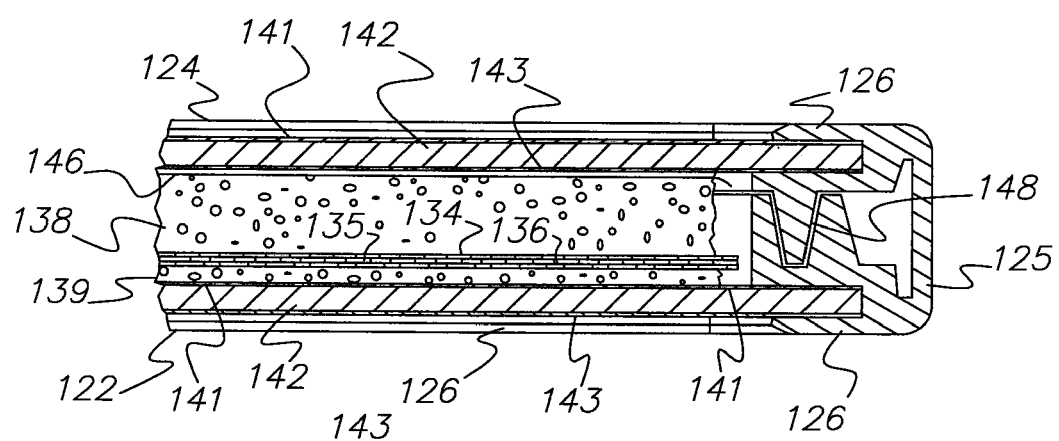
FIG. 9 is a partially sectional, elevational view taken along lines 9-9 in FIG. 6.

FIG. 9 is a partial cross-sectional view of cassette 120 taken along line 9-9 in FIG. 6, illustrating the construction of cassette 120 in the area of hinged border 125. The front and back panels 122 and 124 include a polypropylene core 142 sandwiched between two thin skins of aluminum 141, 143. A urethane border 126 is formed on the outside edges of panels 122 and 124. The border 126 includes hinge 125 which has contours 148 that create lightlock features. Radiographic photothermographic sheet media (x-ray film) 135 is sandwiched between intensifying screens 134, 136 and resilient foam layers 138 and 139 that apply force to intensifying screens 134 and 136. Lead foil 146 is also provided in contact with foam layer 138.

As shown in FIGS. 6 and 7, cassette 120 has an information member 160 associated with it. Information member 160 can be a bar code, a magnetic member, an electrical touch member, an RFID transponder, or the like. The information member can be located anywhere on or in cassette 120 that allows communication with it from outside cassette 120. An RFID transponder is preferable since it can be placed anywhere inside or on the outside of cassette 120.

Figure 30:
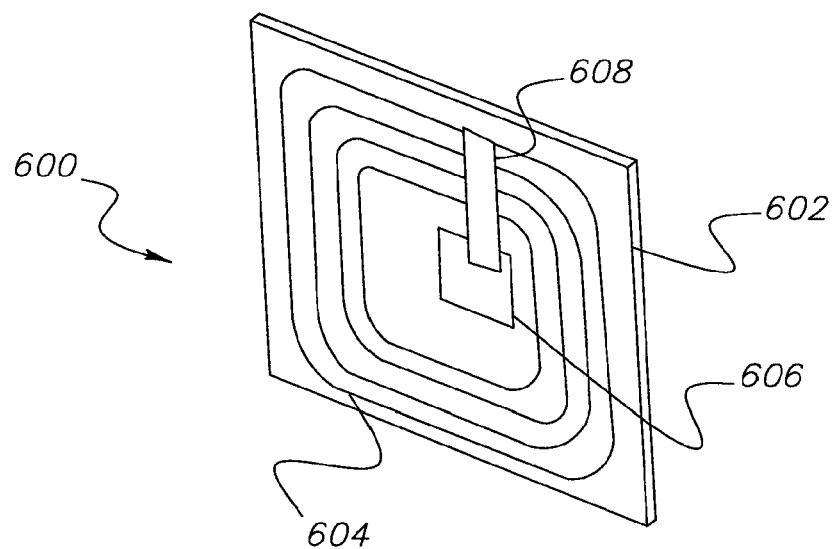
FIG. 30 is a diagrammatic view of an RFID transponder.

Radio frequency identification (RFID) transponders are well known and widely available in a variety of forms. Inlay transponders have a substantially flat shape. FIG. 30 shows an exemplary RFID transponder 600 suitable for use with the system of the present invention. As shown, transponder 600 has a flexible support sheet 602 carrying a planar flat coil antenna 604 and an integrated circuit chip 606 having a nonvolatile digital memory such as an EEPROM (Electrically Erasable Programmable Read-Only Memory). Stored in nonvolatile memory are relevant encoded digital data. Support sheet 602 is electrically insulating plastic and antenna 604 is a layer of conductive material deposited on sheet 602. Connectors 608 and necessary insulation are provided as deposited layers. Inlay transponders of this type are marketed by Texas Instruments Inc., Dallas, Tex. as Tag-itTM inlays. Transponders supplied from other sources may also be used. The transponder is interrogated by a radio frequency (RF) wireless signal from an external transceiver, which need not be in physical contact with the transponder and can be some distance from it. Transponder 600 has a unique ID code which is transmitted to the transceiver upon interrogation. Data can be both written to and/or read from the transponder memory. Other transponder configurations can also be used.

A suitable communication device is provided either with or associated with printer 30 to effect communication between cassette 120 and processor 30. For example, the communication device can be located in or on processor 30 to communicate with a cassette received by processor 30. Alternatively, a hand held or table mounted device, such as a bar code reader, can be used to transfer digital data from the information member to the reader and the digital data subsequently transferred to processor 30.

Figure 10:
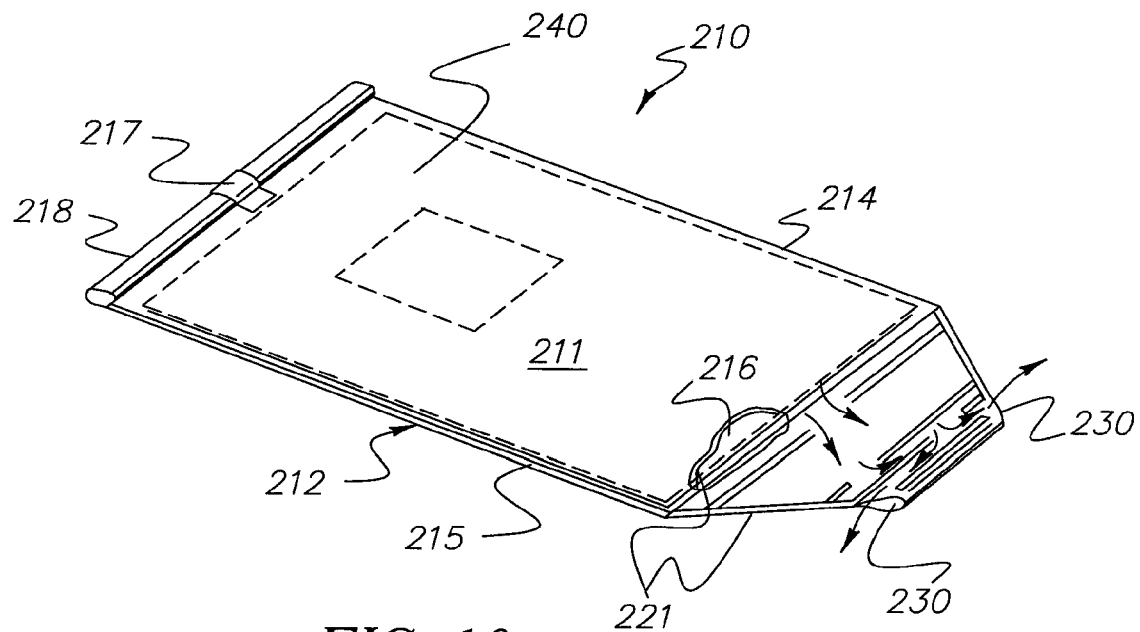
FIG. 10 is a perspective view of a flexible media package that can be used in carrying out the present invention.

Media package 28 contains a stack of unexposed radiographic photothermographic sheet media in a light tight environment. Media package 28 can be a flexible package, as shown in FIG. 10 and described in greater detail in U.S. Pat. No. 5,973,768. As shown, packaging 210 includes a light tight bag of flexible material such as low density polyethylene and having top member 211 and lower member 212. Members 211 and 212 are sealed along their long edges by seals 214 and 215. Unexposed photothermographic sheet media 216 are stacked in packaging 210. One end 218 of members 211 and 212 are folded over and held by tape 217. The back end 221 is sealed with a plurality of offset seals (not shown) that provide a light tight seal but allow air to escape from the interior of packaging 210 through holes 230.

Packaging 210 is provided with an information member 240 that can be a bar code, a magnetic member, an electrical touch member, an RFID transponder, or the like. The information member stores relevant digital information, such as, packaging ID number, sheet media size, sheet media speed, sheet media manufacturer's originated processing conditions, manufacturer's name, date of sheet media manufacture, or the like. The information member 240 can be located anywhere inside or outside packaging 210 that allows communication with it from outside cassette 10. An RFID transponder is preferable since it can be placed anywhere inside or on the outside of packaging 210. A suitable communication device is provided either with or associated with printer 30 to effect communication between packaging information member 240 and processor 30. For example, the communication device can be located in or on processor 30 to communicate with packaging 210 received by processor 30. Alternatively, a hand held or table mounted device, such as a bar code reader, can be used to transfer digital data from the information member to the reader and the digital data subsequently transferred to processor 30.

Figure 11:
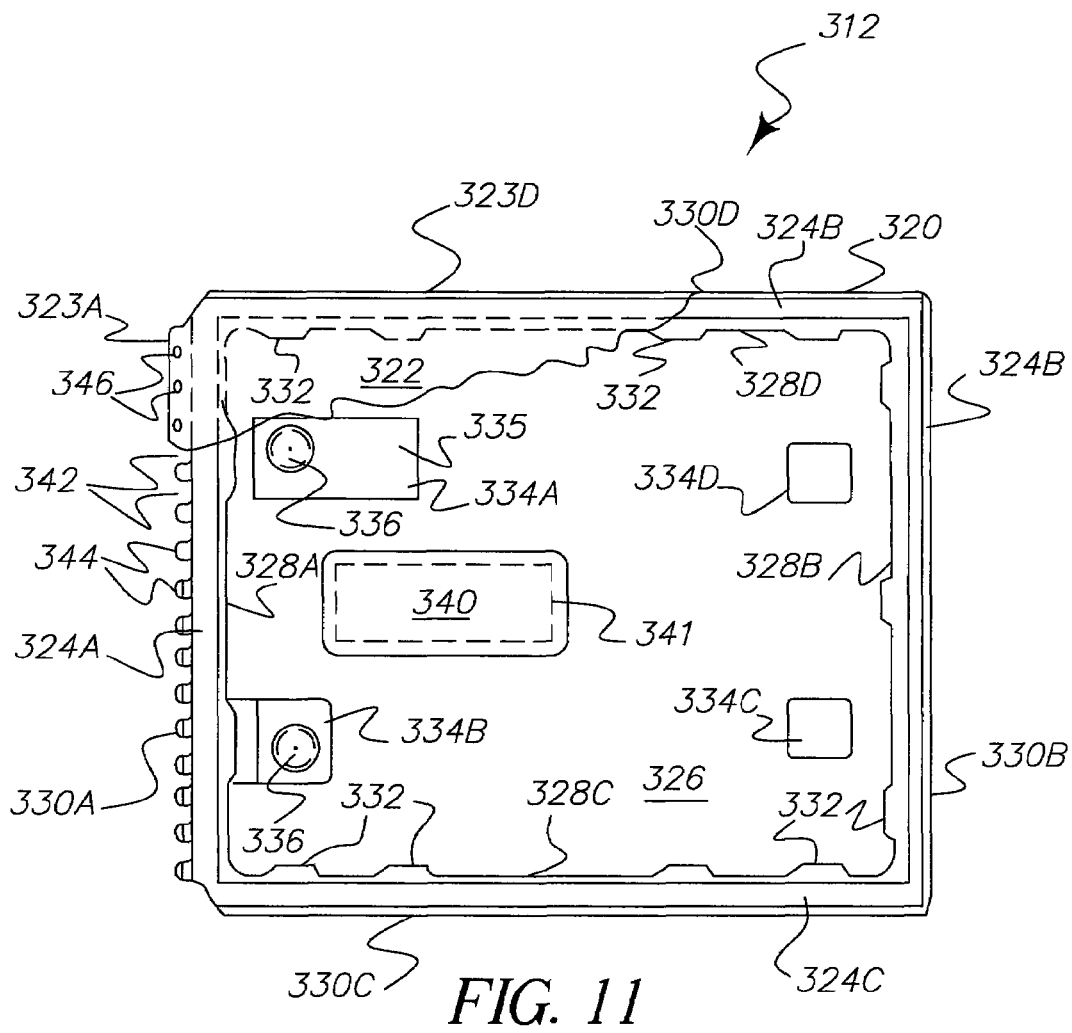
FIGS. 11 and 12 are respective top plan and side elevational views of a sheet media cartridge that can be used in carrying out the present invention.
Figure 12:
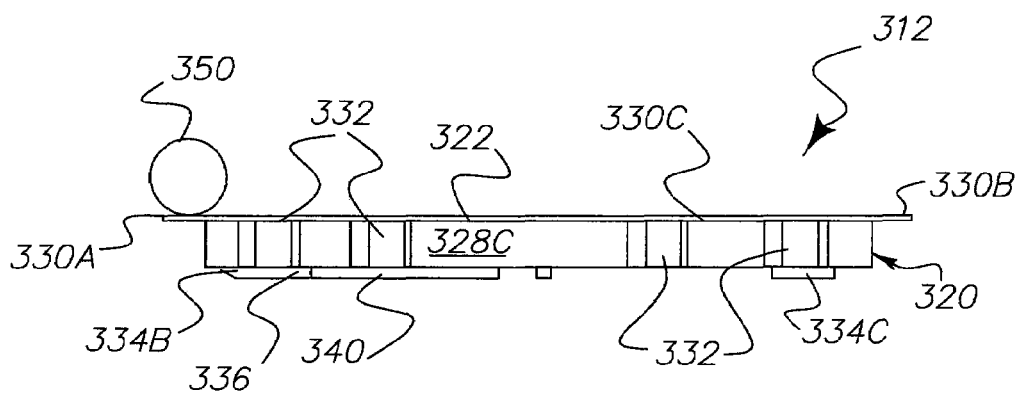

Packaging for media sheets can also take the form of a resealable rigid cartridge disclosed in U.S. Pat. No. 5,473,400, issued Dec. 5, 1995, inventors Lemberger et al. As shown in FIGS. 11 and 12, resealable cartridge 312 includes an optically opaque rigid polymer tray 320 and a flexible opaque polymer cover 322. Tray 320 receives a stack of unexposed radiographic photothermographic sheet media. Cover 322 is resealably mounted to tray 320 by adhesive strips 324A-324D. Tray 320 is a relatively shallow member and includes a generally planar bottom wall 326, front wall 328A, rear wall 328B, and side walls 328C and 328D. Lips 330A-330D extend outwardly from the upper edges of respective walls 328A-328D, and circumscribe a media access opening of tray 320. Inwardly projecting guides 332 are formed on walls 328A-328D to properly position media sheets within tray 320. Feet 334A-334D are provided to support cartridge 312. Positioning recesses 336 help to orient cartridge 312. Media presence monitoring well 335 allows sensors to extend into well 335 when all media has been removed from tray 320. A recess 340 in bottom wall 326 receives an information member 341, such as a bar code or RFID transponder. A bar code would be located on the outside of cartridge 312, an RFID transponder can be located anywhere on the inside or outside of cartridge 312 itself or on an insert located below the stack of sheet media. The RFID transponder can be communicated with wirelessly by means of an RFID transceiver.

The leading edge of front lip 330A includes a series of evenly spaced cutout sections 342 between projections 344 which cooperate with an opening and closing mechanism 350 described in greater detail in U.S. Pat. No. 5,473,400, the contents of which are hereby incorporated by reference.

Cover 322 is a flexible, photo inert and optically opaque sheet of material sized to extend over the access opening of tray 320. Cover 322 has edges 323A-323D which extend between and mate with tray lips 330A-330*d*, respectively. Opening and closing mechanism 350 rolls up and unrolls the front edge of cover 322 to allow removal of a sheet media from cartridge 312 and to reseal cartridge 312.

Figure 13:
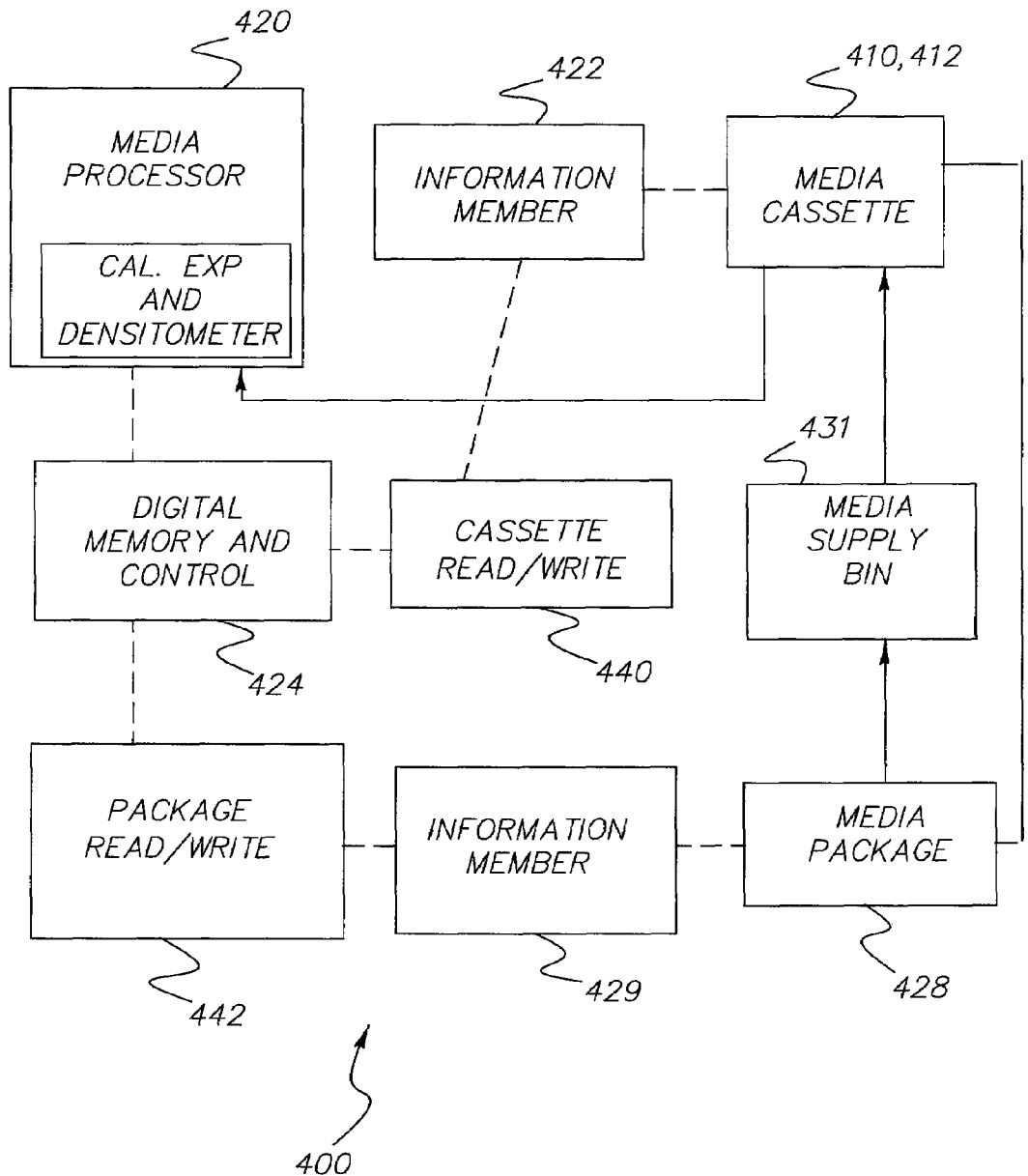
FIG. 13 is a block diagram of still another embodiment of the present invention.

Referring now to FIG. 13, there is shown another embodiment of the present invention particularly suited to the manual loading of radiographic photothermographic sheet media into a cassette and the manual loading of the exposed media into a thermal media processor. As shown, the image quality control system 400 includes thermal media processor 420 having digital memory and control 424, photothermographic sheet media package 428 having associated information member 429, media supply bin 431 for holding supplies of unexposed sheet media, and cassette 410 with associated information member 422, for containing a single sheet media 412 which has been exposed to a radiographic image and which is to be subsequently processed by media processor 420. Thermal media processor 420 is preferably that described with reference to FIGS. 4 and 5, but can be any suitable thermal processor well known to those skilled in the art, such as a heated drum processor disclosed in U.S. Pat. No. 6,007,971.

Cassette read/write device 440 communicates information between processor digital memory and control 424 and cassette information member 422. Cassette read/write device 422 can be an integral part of processor 420 or can be a separate handheld or tabletop device. Media package read/write device 442 communicates information between media package information member 429 and processor digital memory and control 424. Device 442 can also be either an integral part of processor 420 or a separate handheld or tabletop device. Information members 422 and 429 preferably include RFID transponders and devices 440 and 442 include RFID transceivers that can have wireless communication with the RFID transponders of information members 422 and 429.

The operation of system 400 will be more fully explained with reference to the diagrammatic views shown in FIGS. 14-27. FIGS. 14-21 illustrate the media processing operation and FIGS. 22-27 illustrate the calibration operation. Throughout the following description reference is made concurrently to FIG. 13 for identification of components of system 400 which may be referred to but which is not duplicated in FIGS. 14-27.

Figure 14:
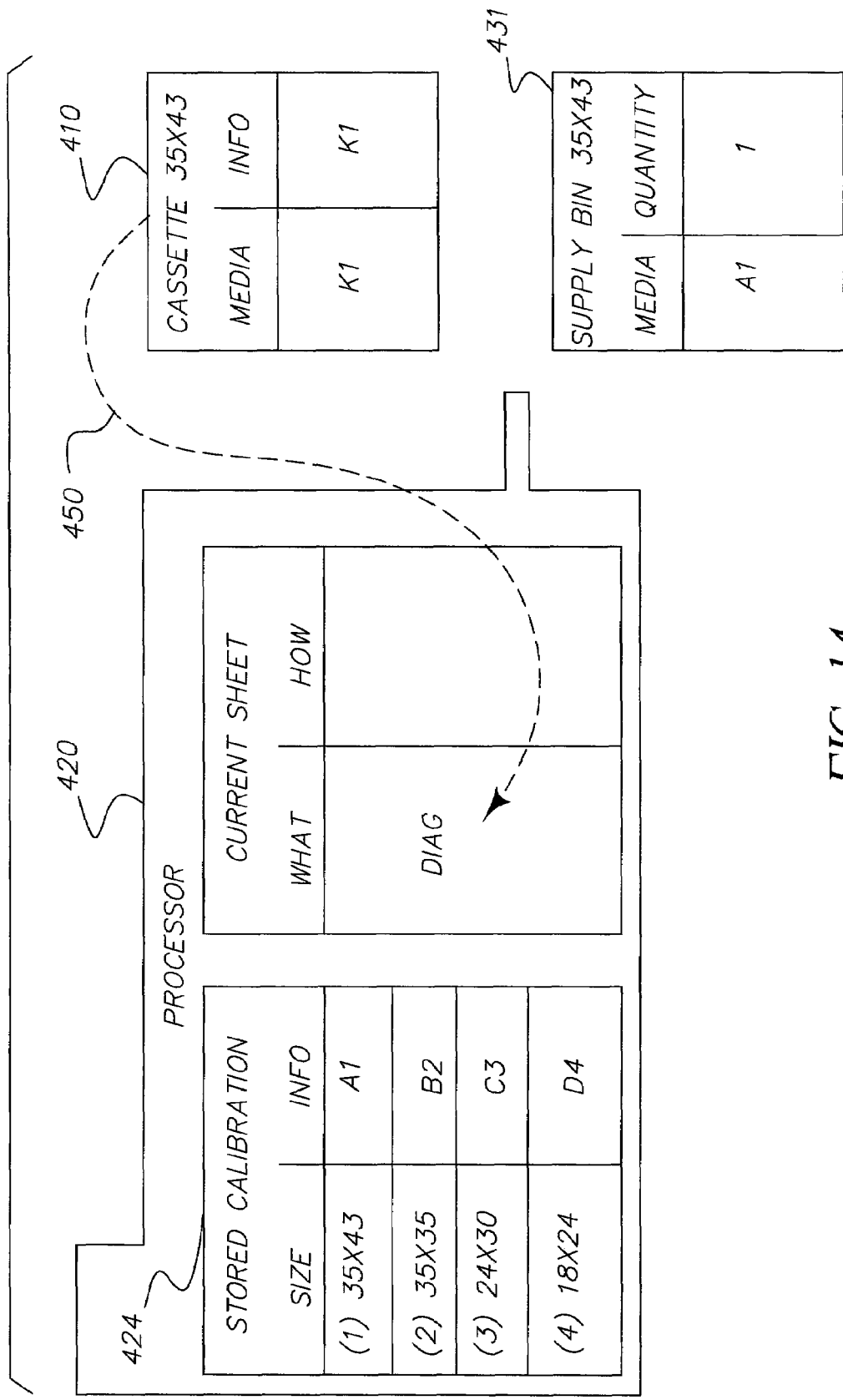
FIGS. 14-21 are diagrammatic views illustrating an embodiment of the present invention.

As shown diagrammatically in FIG. 14, media processor 420 has stored in memory and control 424, digital information representing the calibration processing conditions for four sizes of sheet media that can be processed by processor 420. Thus, the stored information for size 1 (35 cm.×43 cm.) is represented by A1, for size 2 (35 cm.×35 cm.) is represented by B2, for size 3 (24 cm.×30 cm.) is represented by C3, and for size 4 (18 cm.×24 cm.) is represented by D4. Cassette 410 contains an exposed sheet media K1 of size 1 (35 cm.×43 cm.). Stored in cassette information member 422 is information relating to cassette ID, sheet media size, and sheet media calibrated processing conditions. Supply bin 431 holds unexposed sheet media of size 1 with calibrated processing conditions A1, the same stored in processor memory and control 424 for size 1. One sheet media of size 1 remains in supply bin 431. It will be noted that size 1 sheet media contained in cassette 410 is from a different media package and therefore has different sheet media processing conditions stored in cassette information member 422.

Figure 15:
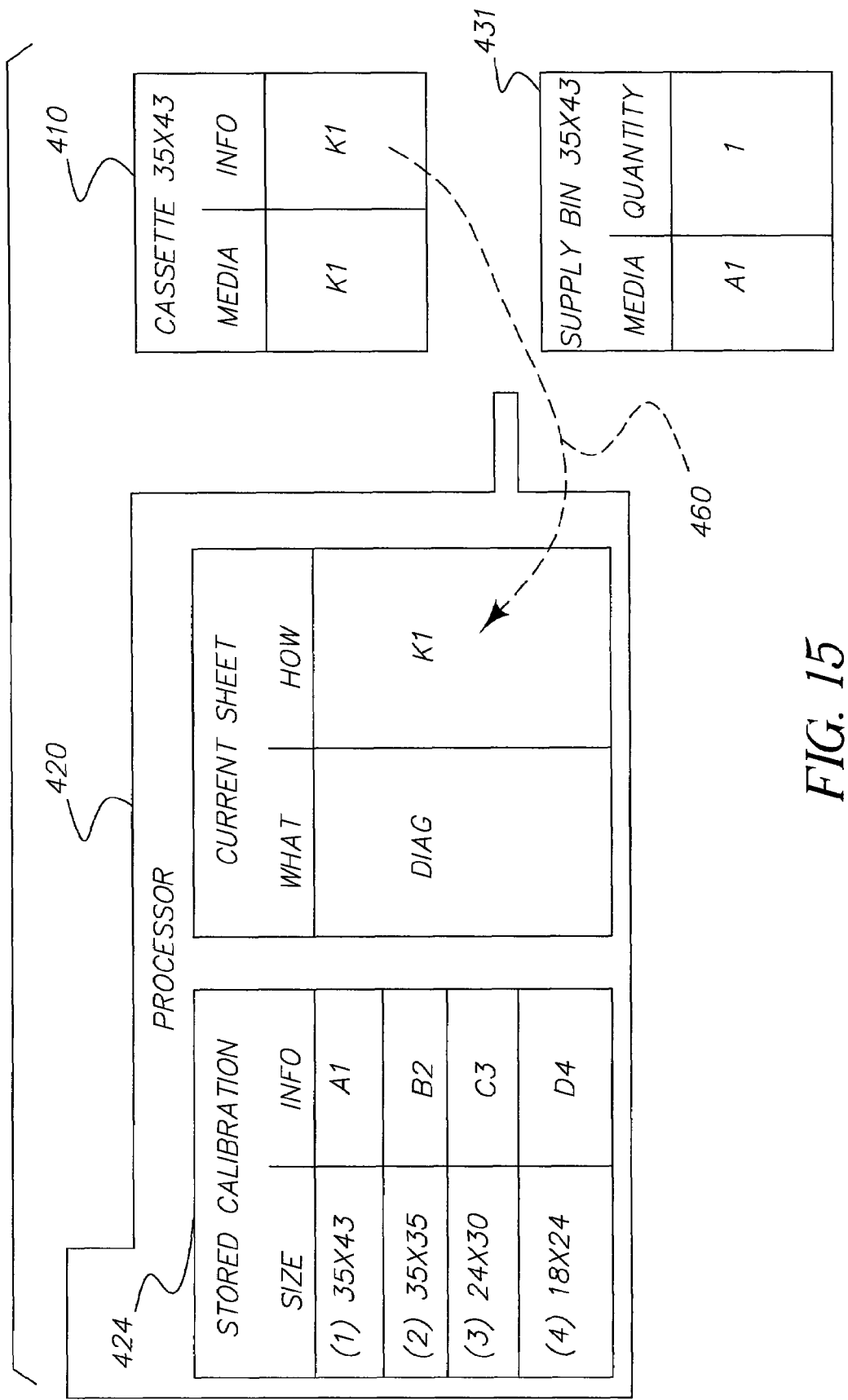

As shown in FIG. 14, the user scans cassette information member 422 with device 440 for cassette ID and sheet media size. This information tells the processor (arrow 450) 420 that the next sheet media to be processed will be a size 1 diagnostic sheet media and not a calibration sheet media (to be explained in greater detail later with reference to FIGS. 22-27). As shown in FIG. 15, device 440 is used to scan cassette information member 422 for the calibrated processing conditions to be used on the exposed sheet media in cassette 410. For the media processor of FIGS. 4-5, such information could include preheat processing temperature, dwell processing temperature, cooling processing temperature, dwell processing time, and non-processing transport speeds. The information K1 is shown by the dotted arrow 460 to be transferred from cassette 410 to processor 420.

Figure 16:
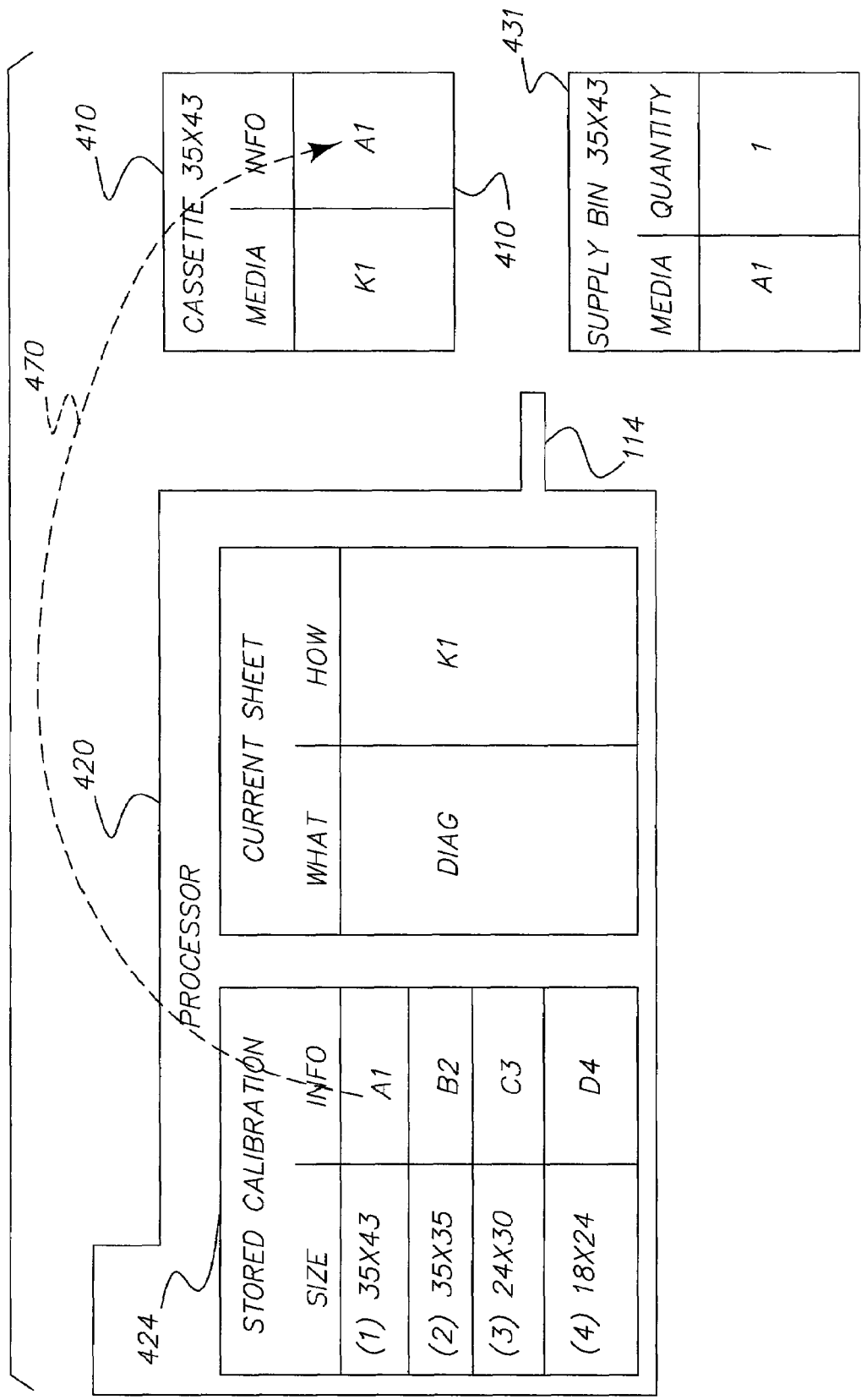
Figure 17:
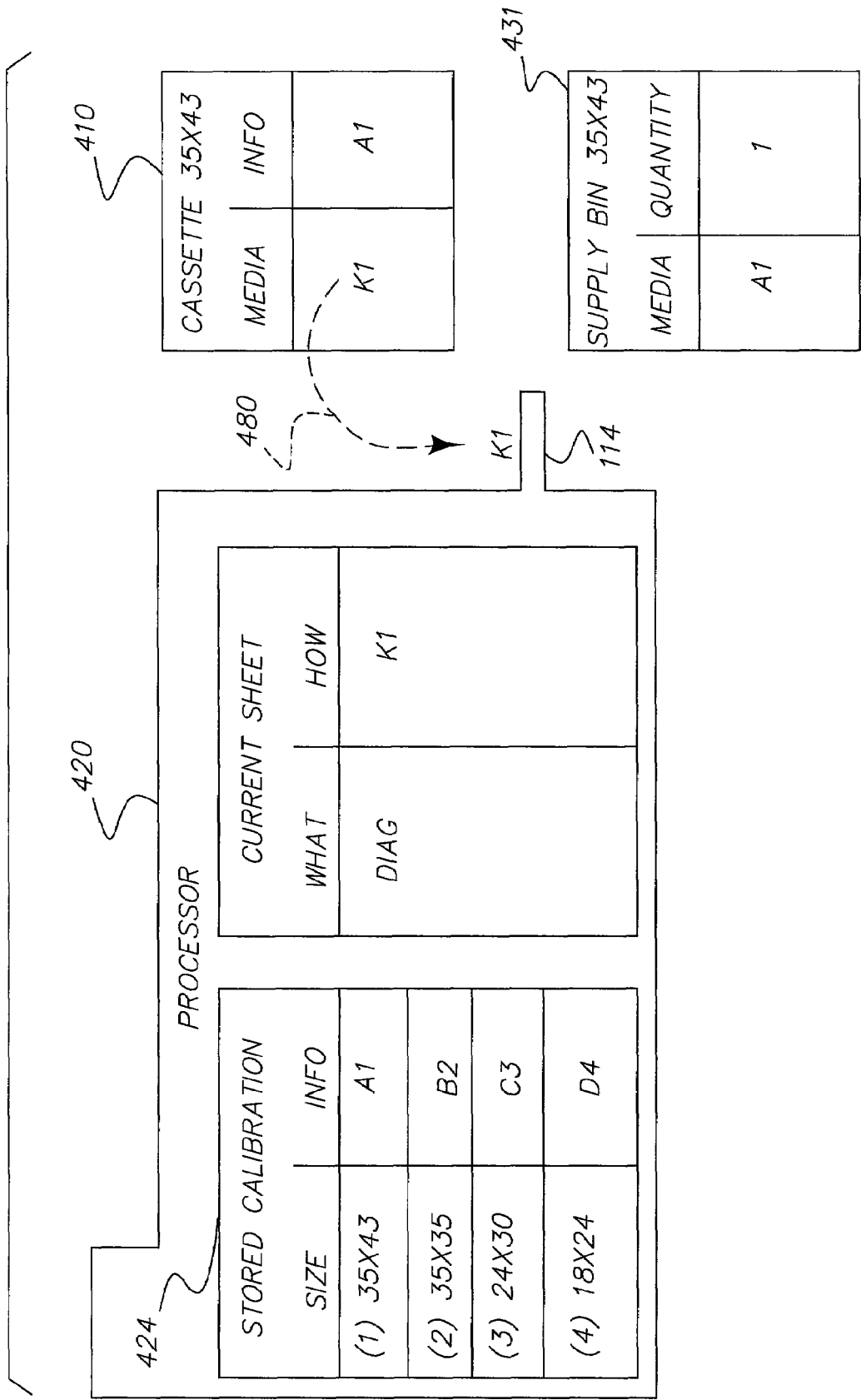
Figure 18:
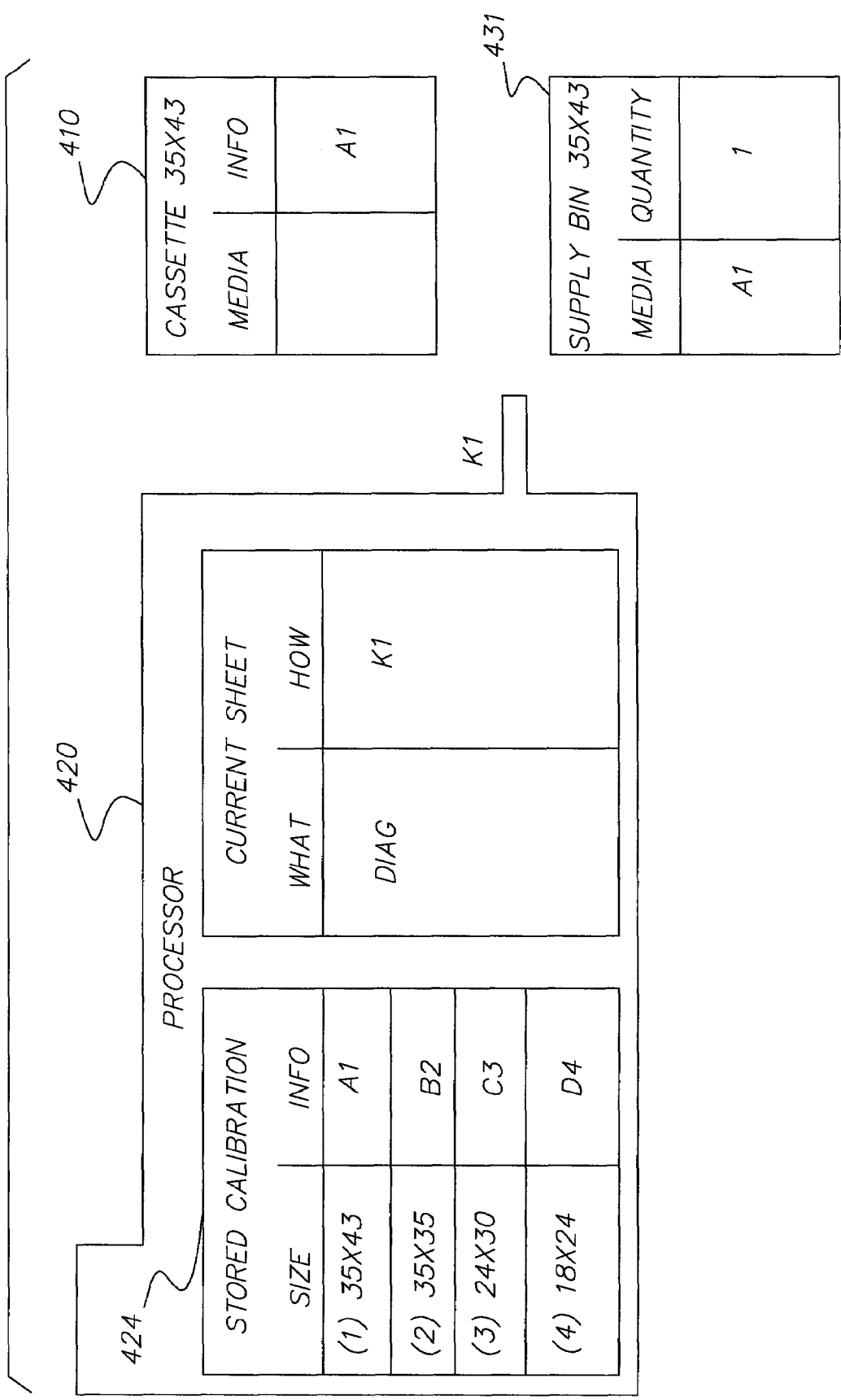
Figure 19:
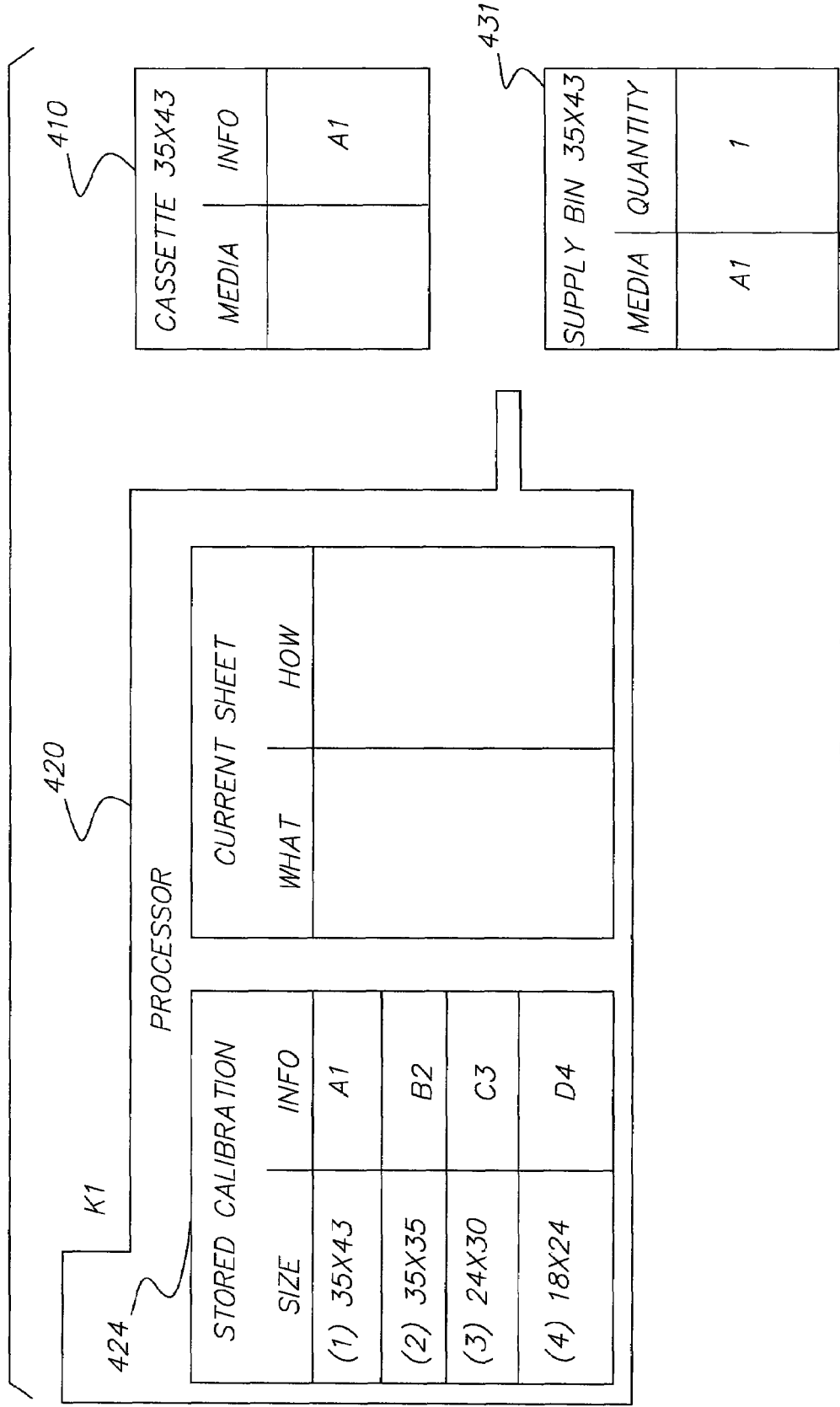

As shown in FIG. 16, the calibrated processing information A1 for the current open supply package for the current size 1 of the sheet media in cassette 410 is written by device 440 from processor memory and control 424 to cassette information member 422 (arrow 470). As shown in FIG. 17, the user removes the exposed diagnostic sheet media K1 from cassette 410 and presents it to receiving section 114 (FIG. 5) of processor 420 (arrow 480). Note that the calibrated processing conditions K1 stored in processor 420 matches the sheet media K1 presented to processor 420. As shown in FIG. 18, processor 420 measures the size of the sheet media K1 presented to processor 420 and compares it to the size of sheet media read from cassette information member 422. If the size information is confirmed, the exposed sheet media K1 is processed correctly and returned to the user (FIG. 19). The diagnostic cassette 410 is now empty of sheet media.

Figure 20:
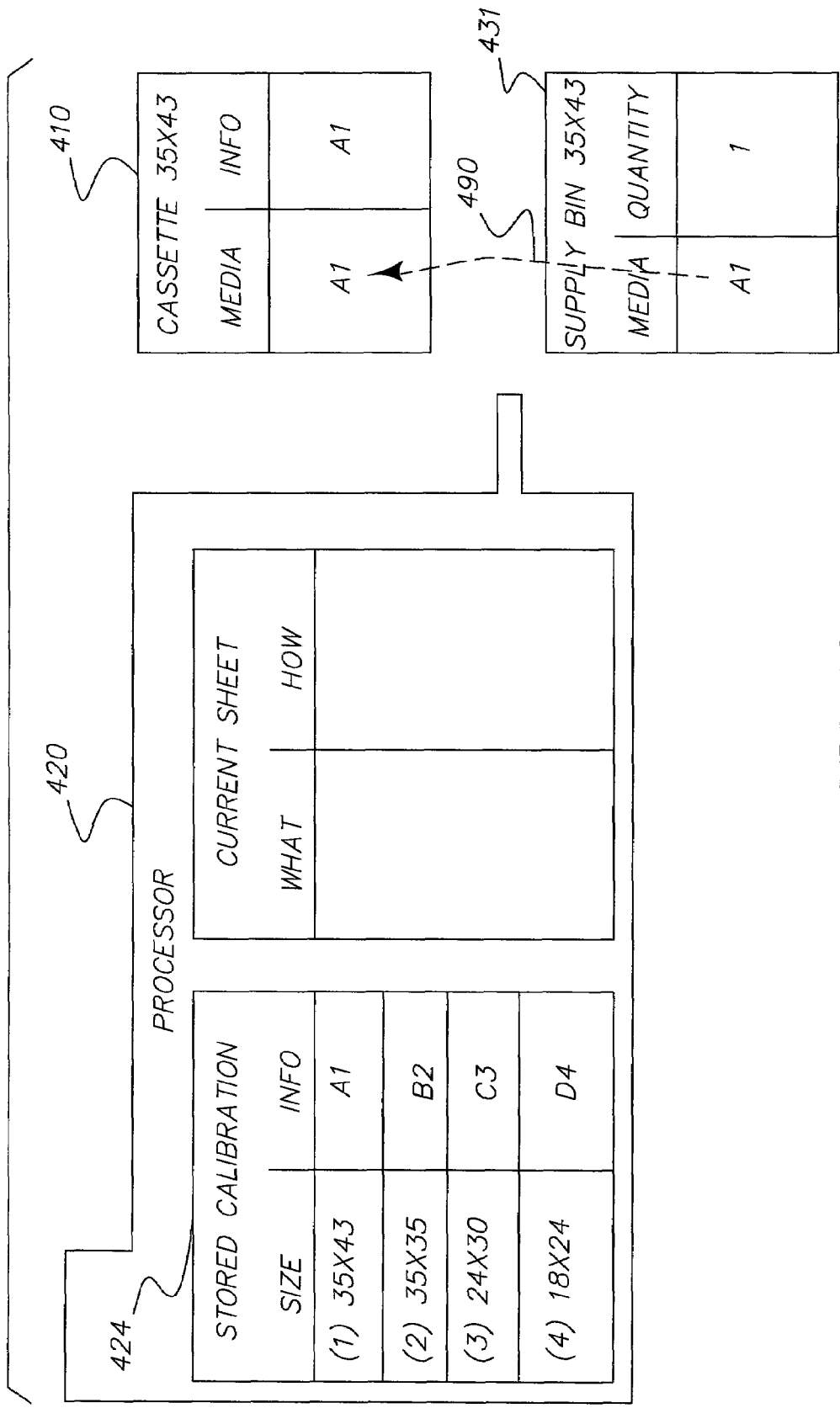
Figure 21:
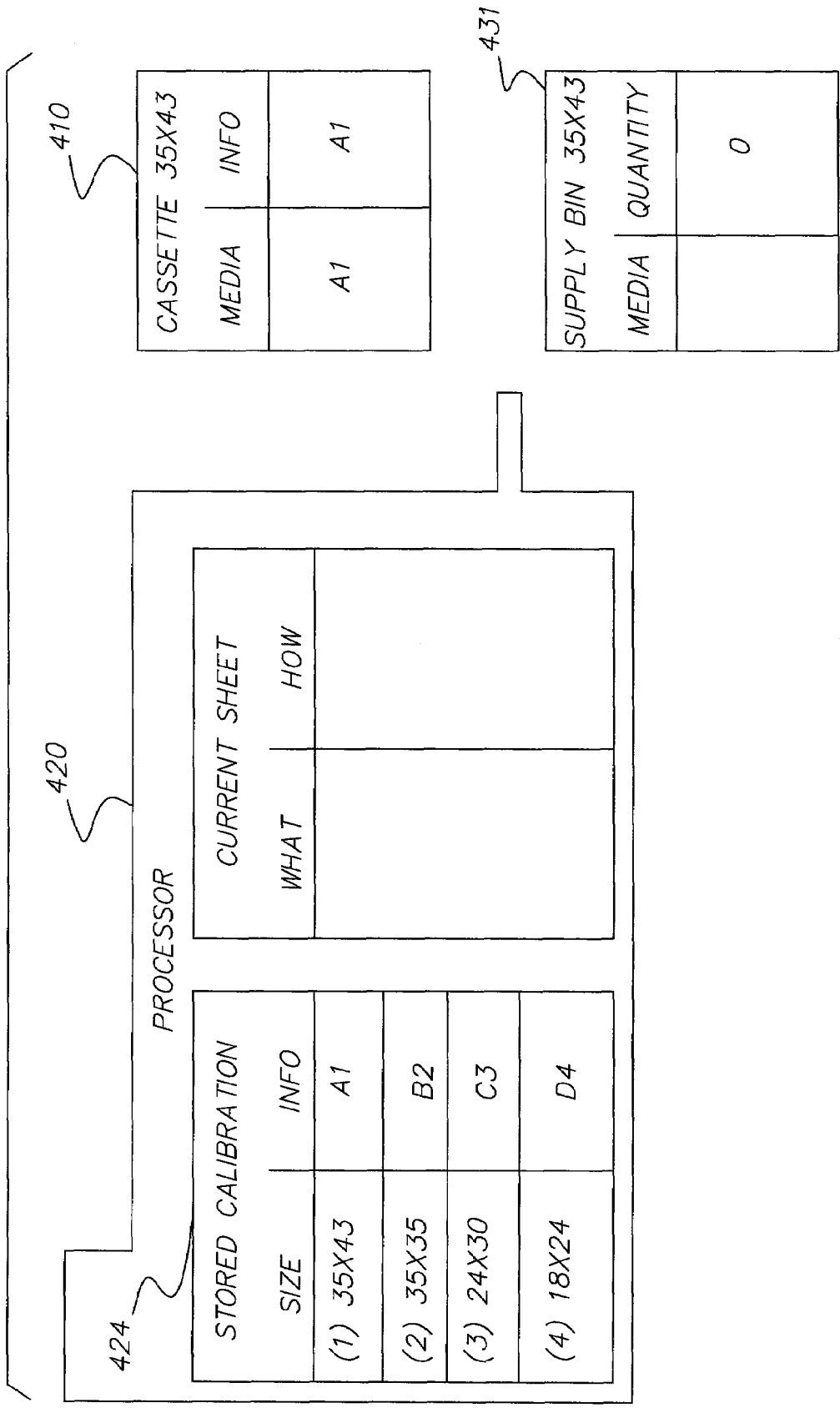

As shown in FIG. 20, the user removes the last unexposed sheet media A1 from supply bin 431 and places it in cassette 410 (arrow 490). Note that the sheet media A1 matches the calibrated processing conditions A1 that have been stored in information member 422 (See FIG. 16). The unexposed sheet media is now ready to be exposed to a radiographic image. As shown in FIG. 21, supply bin 431 is now empty of sheet media of size 1 (35 cm.×43 cm.).

Figure 22:
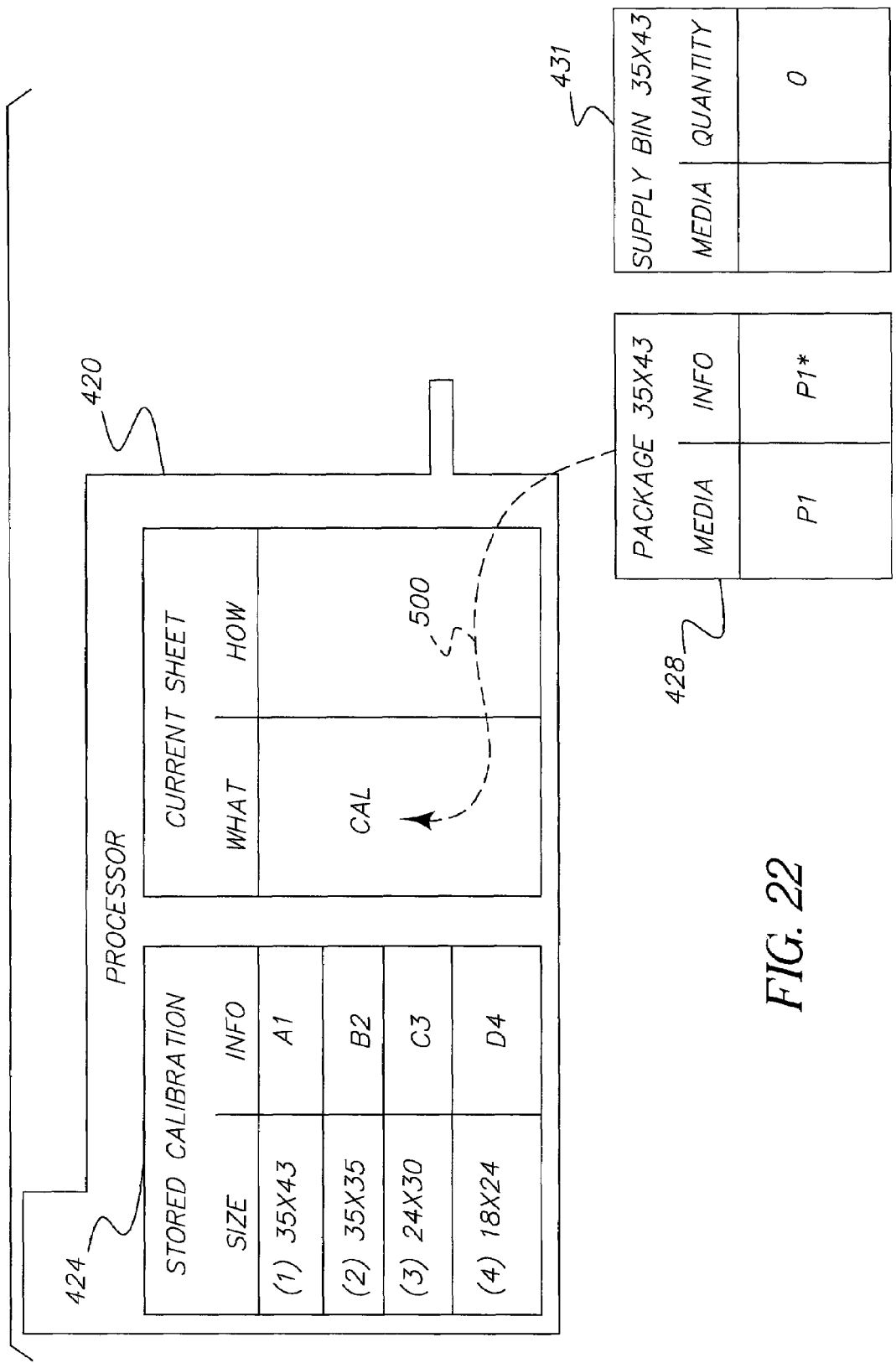
FIGS. 22-27 are diagrammatic views illustrating the calibration feature of the present invention.

Referring now to FIGS. 22-27, there will be described how calibrated processing conditions for a new stack of radiographic photothermographic sheet media to be placed in supply bin 431 are determined according to an embodiment of the present invention. Reference is also made concurrently to FIG. 13. As shown in FIG. 22, a user scans information member 429 of unexposed sheet media package 428 by device 442 to inform the processor 420 (arrow 500) that the next sheet media to be processed by processor 420 will be a calibration sheet media of size 1 (35 cm.×43 cm.). Sheet media package 428 can be of the flexible type shown in FIG. 10, a resealable cartridge shown in FIGS. 11-12, or any other package known to those skilled in the art. Package 428 contains a stack of sheet media P1 of size 1. The first sheet media removed from package 428 is a calibration sheet media. Information member 429 of media package 428 stores manufacturer's originated processing conditions P1*. Size 1 supply bin 431 is shown as empty.

Figure 23:
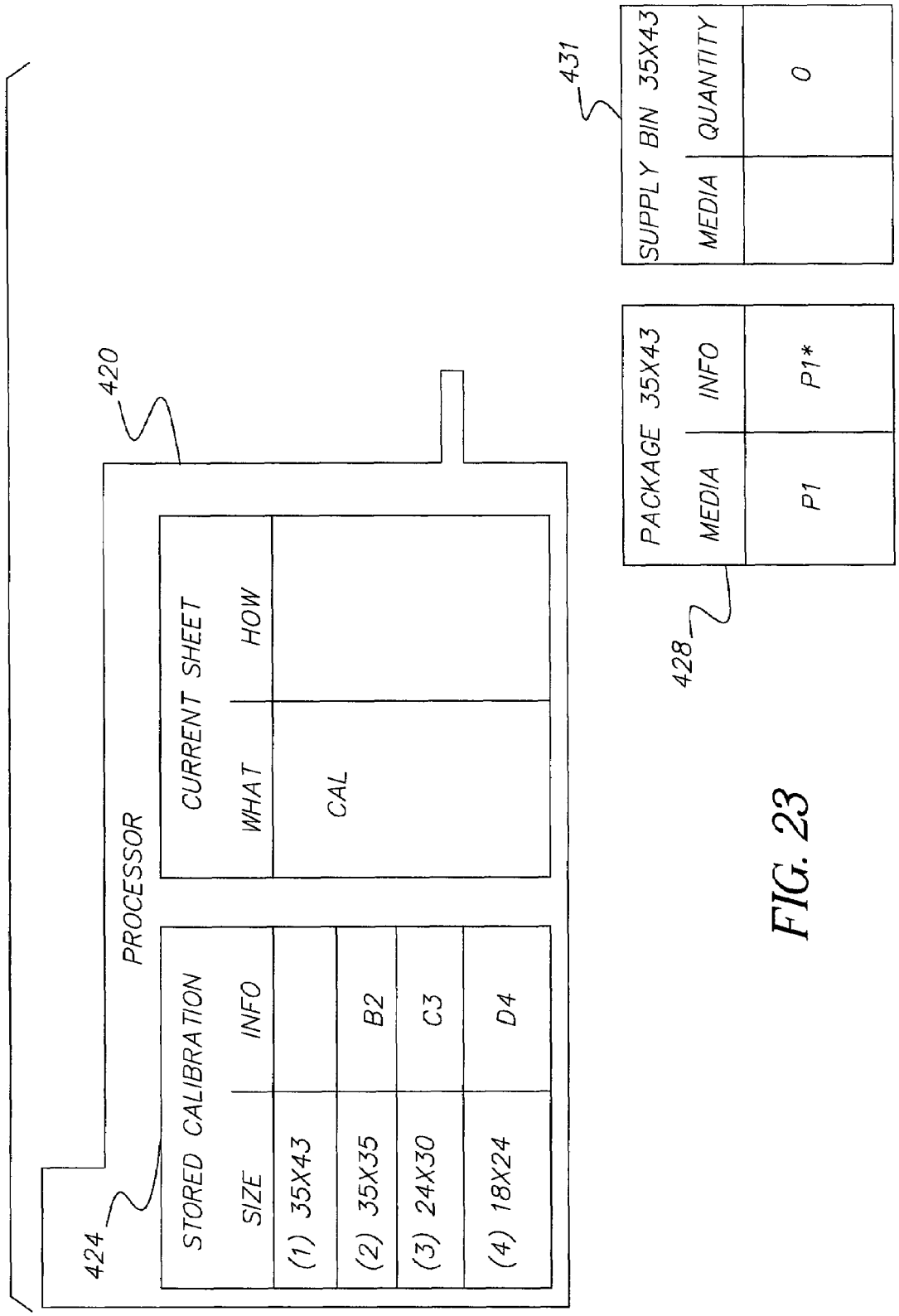
Figure 24:
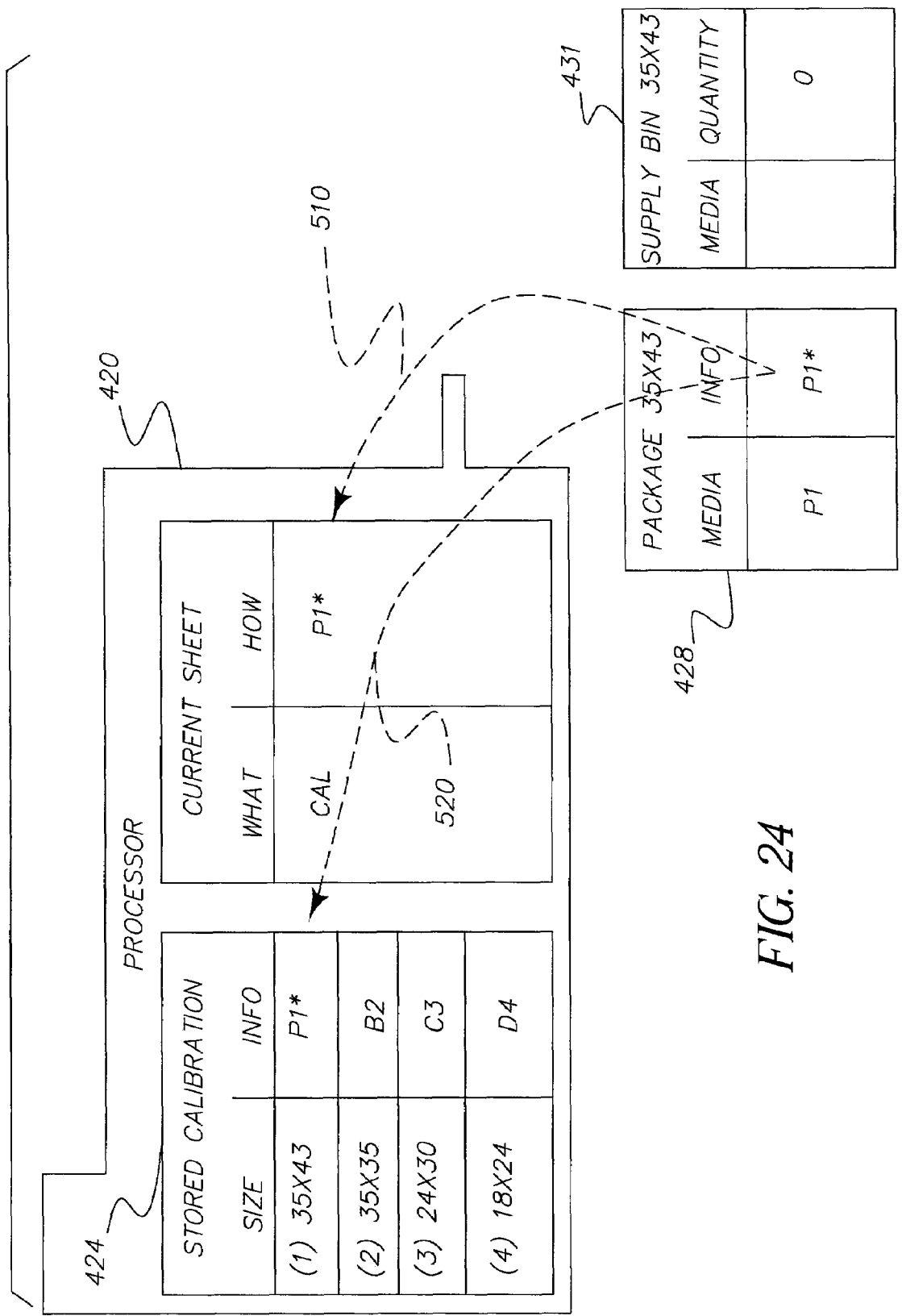

As shown in FIG. 23, the stored calibration processing conditions for the previous sheet media A1 is erased from processor digital memory and control 424. As shown in FIG. 24, device 440 transfers the manufacturer's originated processing conditions P1* from package information member 429 to processor digital memory and control 424 to replace the A1 information and to tell processor 420 what conditions to use in processing the calibration sheet media P1 (arrows 510, 520). The manufacturer's originated processing conditions can include, among others: calibration exposure levels, preheat processing temperature, dwell processing temperature, cooling processing temperature, dwell processing time, correction lookup table, and non-processing transport speeds. Note that the processor 420 does not have the calibrated processing conditions (as opposed to the manufacturer's processing conditions) at this time.

Figure 25:
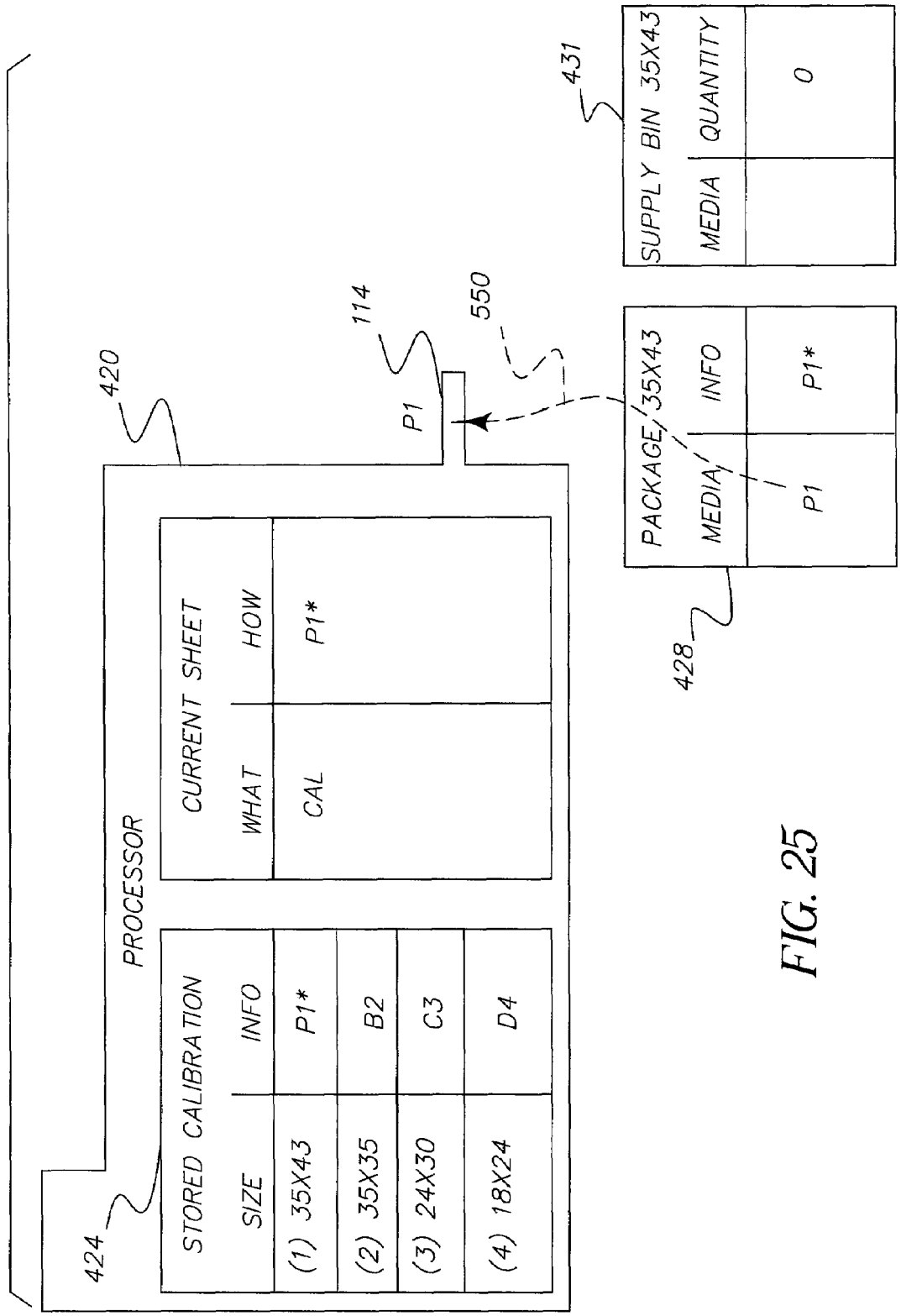

As shown in FIG. 25, the user removes the first sheet of unexposed sheet media P1 from package 428 and presents it (arrow 550) to the processor receiving station (FIG. 5, component 114). Note that the processing conditions P1* stored in processor 420 matches the sheet media P1 at station 114. The processor 420 measures the size of sheet media P1 and compares it to the size read from the package information member 429 to confirm that they are identical.

In one embodiment of the invention, the calibration sheet media in package 428 can be preexposed with a step density pattern of different densities. In the preferred embodiment of the invention, processor 420 is provided with an exposure device, in advance of the thermal processor, to expose unexposed calibration sheet media P1 to a step density pattern of different densities. Processor 420 is also provided with a densitometer located after the sheet media has been processed to measure densities of the step density pattern. (See FIG. 5).

Figure 26:
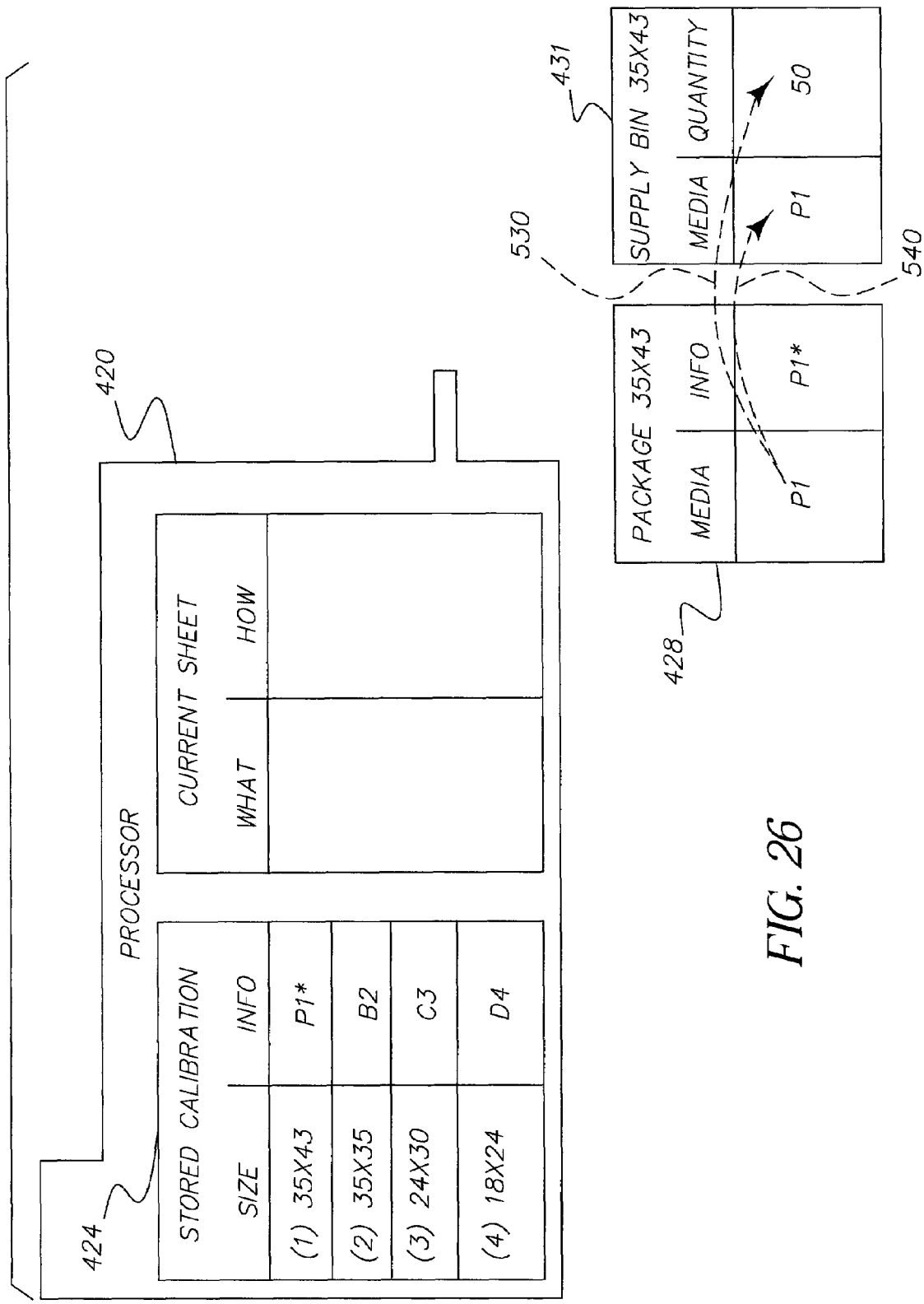

As shown in FIG. 26, the user places the remaining unexposed sheet media P1 (e. g., 50 sheets) from package 428 into supply bin 431 (arrows 530 and 540).

Figure 27:
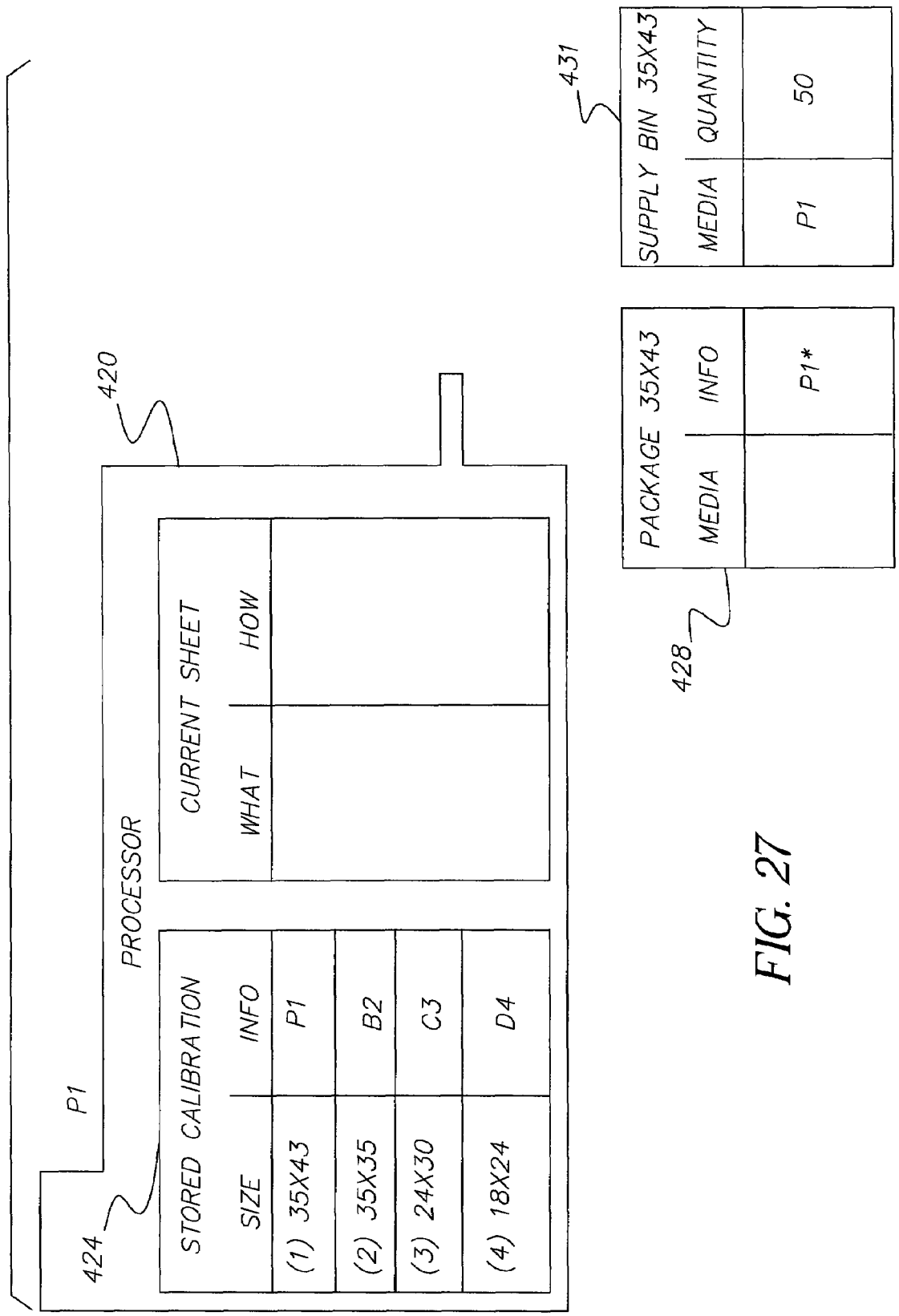

As shown in FIG. 27, the calibration sheet is processed per the P1 processing conditions. The calibration exposure densities are measured and the results compared to the expected densities lookup table. Any variations in density are used to modify the manufacturer's originated processing conditions P1* to produce calibrated processing conditions P1 which are stored in digital memory and control 424 of processor 420 for sheet media size1 in place of processing conditions P1*. The processed calibration sheet P1 is then returned to the user.

Further refinement to this calibration technique could include providing a density patch on each subsequent sheet media in the package and reading the density of the patch to modify the processing conditions of subsequent sheet media to compensate for additional media changes, such as decrease in media speed, during use of the remaining sheet media in the package. Another refinement would be to calibrate the first sheet in a package and adjust the processing conditions for remaining sheet media based on media age or environmental conditions.

Instead of manually removing a sheet media from a cassette and presenting it to the processor for processing and instead of manually reloading the cassette with unexposed sheet media, these operations can be done automatically through the use of a multiloader. A multiloader is a device into which a cassette with exposed sheet media is inserted. The cassette is then automatically opened, the sheet media removed and then sent to a processor. Concurrently a new sheet media is removed from a sheet media supply and placed in the open cassette. The cassette is then closed and returned to the customer.

Figure 28:
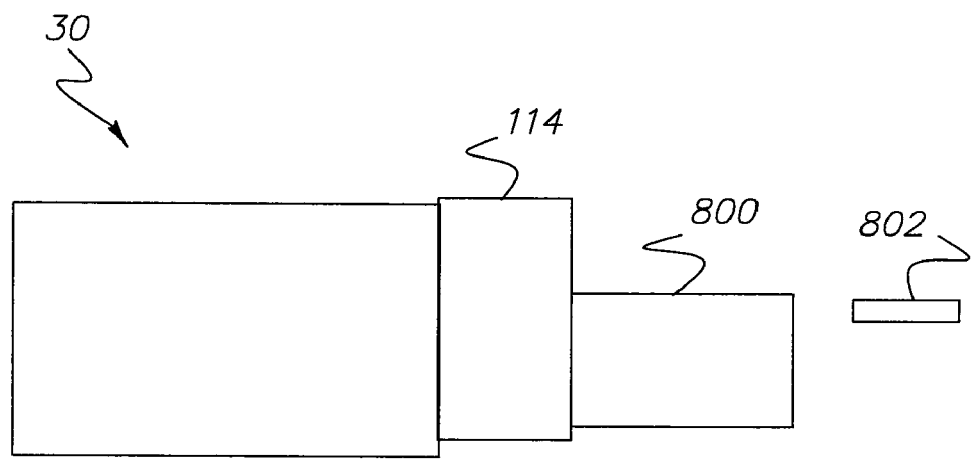
FIG. 28 is a block diagram of another embodiment of the present invention incorporating the use of a sheet media multiloader.
Figure 29:
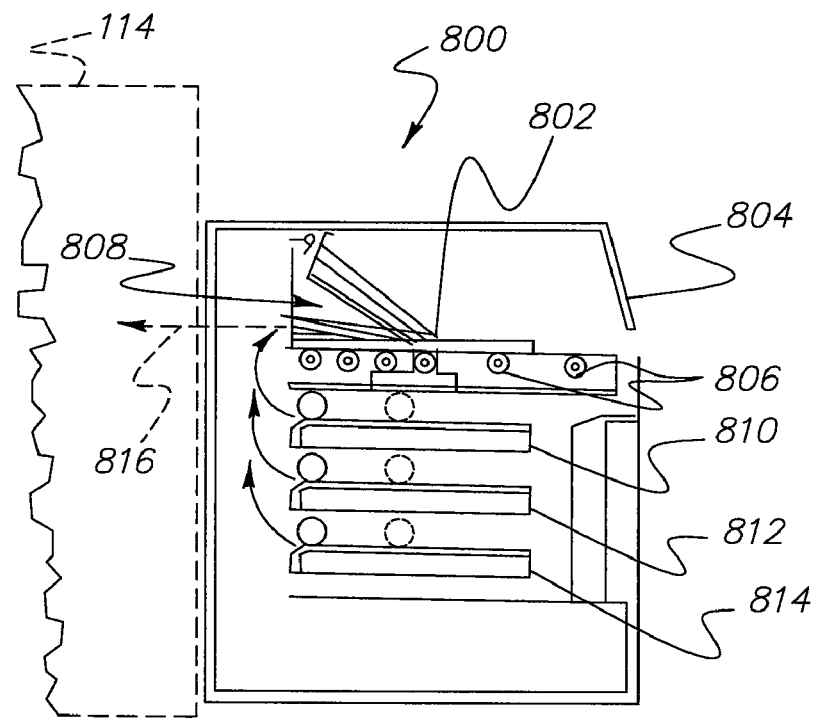
FIG. 29 is a diagrammatic view of an exemplary multiloader for use in the embodiment of FIG. 28.

Referring now to FIGS. 28 and 29 there will be described a multiloader that can be used in carrying out the present invention. As shown in FIG. 28, media processor 30 having media receiving station 114 has a multiloader 800 located in communication with receiving station 114 to present exposed sheet media to processor 30 for processing. A cassette 802 containing exposed sheet media is shown about to be loaded into multiloader 800. As shown in FIG. 29, multiloader 800 includes an inlet opening 804 for receiving a cassette 802 containing exposed radiographic sheet media. Rollers 806 feed cassette 802 to cassette unloading and loading station 808. Multiloader 800 is provided with sheet media supply areas 810, 812, and 814. Which supply unexposed sheet media to be loaded into an empty cassette 802. Supply areas 810-814 can hold sheet media of different sizes and types. For example, supply area 810 can be configured to receive radiographic sheet media of one size, e. g., 35 cm.×43 cm., supply area 812 can be configured to receive radiographic sheet media of a second size, e. g., 35 cm.×35 cm., and supply area 814 can be configured to receive radiographic sheet media of a third size, e. g., 24 cm.×30 cm. or 18 cm.×24 cm. More or less supply areas may be provided and all of the supply areas can be configured to receive the same size or type of radiographic sheet media.

Supply areas 810-814 are preferably configured to receive resealable cartridges as exemplified by the cartridge shown in FIGS. 11 and 12. Alternatively, supply areas 810-814 can be configured to receive flexible packaging as shown in FIG. 10. A device would then be provided to remove the flexible packaging from the stack of sheet media. A third alternative is to have supply areas configured as supply drawers which are manually loaded with a stack of sheet media. In any case, multiloader 800 provides a light-tight environment for sheet media received in supply areas 810-814.

In operation, a media cassette 802 is loaded through inlet opening 804 and rollers 806 feed the cassette 802 to cassette unloading and loading station 808. The exposed sheet media is unloaded from cassette 802 after cassette 802 has been opened by means known to those skilled in the art, such as described in U.S. Pat. No. 5,402,997, issued Apr. 4, 1995, inventors Schopple, et al. The exposed sheet media is fed along path 816 to receiving station 114 of media processor 30. Cassette 802 is now empty and ready to receive an unexposed sheet media of the proper size from one of supply areas 810-814. After the unexposed sheet media has been loaded into cassette 802, cassette 802 is closed and transported by rollers 806 back to inlet opening 804 for removal by the user.

Instead of the closed loop approach described above for determining calibrated processing conditions for sheet media, an open loop approach can be used. A predictive formula based on selected inputs is used and assumes that the selected inputs are the most significant predictors of media behavior. Such selective inputs include age of the media, i. e., the time between the manufacture date of the media and the date that the media is used, and initial media speed. A mixed approach would be to calibrate the first sheet media in a package and then recalibrate or adjust processing conditions based on media age.

Although the open loop approach can improve the overall image quality of the processing system, it does not take into account the individual variation in storage conditions (e. g., temperature, humidity) that a package of sheet media may have experienced. In order to compensate for individual storage conditions that a package of sheet media has endured prior to customer use requires the preferred closed loop approach described above.

In this application the term "manufacturer's originated processing conditions" refers to the processing conditions established by the sheet media manufacturer and stored in an information member of a package of sheet media at the time of manufacture. These conditions are considered the ideal processing conditions for that batch of media at the time of manufacture. The term "calibrated processing conditions" refers to the media processing conditions that have been determined at the time of use of the package of sheet media. These conditions may or may not be the same as the "manufacturer's originated processing conditions" and will be determined after use of one of the open loop or closed loop approaches described above.

All documents, patents, journal articles and other materials cited in the present application are hereby incorporated by reference.

The invention has been described in detail with particular reference to certain preferred embodiments thereof, but it will be understood that variations and modifications can be effected within the spirit and scope of the invention.

PARTS LIST 10 cassette
12 radiographic sheet media
14 x-ray source
16 object to x-rayed (body part)
18 radiographic image
20 media processor
22 information member
24 digital memory and control
26 information source
28 media package
29 information member
30 thermal processor
32 imaging media
34 preheat chamber
36 dwell chamber
38 housing
40 entrance
42 exit
44 transport system
46 heating system
48 housing
50 entrance
52 exit
54 transport system
56 heating system
58 transport path
70 upper rollers
72 lower rollers
74 upper heating member
76 lower heating member
78 heat plate
80 heat blanket
82 support shafts
84 cylindrical sleeves of support material
86 temperature sensor
88, 90 exhaust ports
91 external vacuum system
92 transition section
94 guide channel
96 upper rollers
98 lower rollers
100 upper heating member
102 lower heating member
104 heat plate
106 heating blanket
108 temperature sensor
110, 112 exhaust ports
114 receiver section
116 nip rollers
120 cassette
122, 124 panels
125 hinge
126 border
130 latch
134 intensifying screen
135 radiographic sheet media
136 intensifying screen
138, 139 resilient foam layers
141 aluminum skin
142 polypropylene core
143 aluminum skin
146 lead foil
148 contours
160 information member
210 packaging
211 top member
212 lower member
214, 215 seals
216 unexposed photothermographic sheet media
217 tape
218 packaging one end
221 packaging back end
230 holes
240 information member
312 resealable cartridge
320 tray
322 flexible cover
323A-323D edges
324A-324D adhesive strips
326 bottom wall
328A front wall
328B rear wall
328C, 328D side walls
330A-330D lips
332 guides
334A-334D feet
335 media presence monitoring well
336 positioning recesses
340 recess
341 information member
342 cutout sections
344 projections
350 opening and closing mechanism
400 image quality maintenance system
410 cassette
412 media
420 media processor
422 information member
424 digital memory and control
428 photothermographic sheet media package
429 information member
431 media supply bin
440 cassette read/write device
442 media package read/write device
450, 460, 470, 480, 490, 500, 510, 520, 530, 540, 550-arrows
600 inlay RFID transponder
602 flexible support sheet
604 planar flat coil antenna
606 integrated circuit chip
608 connectors
800 multiloader
802 cassette
804 inlet opening
806 rollers
808 cassette unloading and loading station
810, 812, 814 sheet media supply areas
816 path
900 exposure device
902 densitometer

What is claimed is:

1. A system for controlling image quality in processing radiographic photothermographic sheet media, comprising:
a cassette for removably containing radiographic photothermographic sheet media;
an information member associated with said cassette for storing information including size of sheet media contained in said cassette and calibrated conditions for processing said radiographic sheet media contained in said cassette, wherein said calibrated processing conditions include one or more of, preheat processing temperature, dwell processing temperature, cooling processing temperature, dwell processing time, and non-processing transport speeds; and a supply of unexposed sheet media for providing an unexposed media to said cassette when an exposed sheet media has been removed from said cassette for processing by said processor;

wherein said supply includes a package initially containing said unexposed sheet media and includes an information member associated with said package for storing information including sheet media size and manufacturer's originated media processing conditions; wherein said manufacturer's originated media processing conditions include one or more of, calibration exposure levels, correction lookup table, preheat processing temperature, dwell processing temperature, cooling processing temperature, dwell processing time, and non-processing transport speeds;

wherein said package includes a sheet media used for determining calibrated processing conditions for the remaining media sheets in said package;

wherein said processor includes an exposure system for exposing said calibration sheet from said package to a plurality of different density regions and a densitometer for measuring the densities of said plurality of density regions after said calibration media sheet has been processed by said processor according to said manufacturer's originated processing conditions received from said package information member; and wherein said processor includes a digital memory and control system and wherein said control system determines and stores calibrated media processing conditions by modifying said manufacturer's originated processing conditions as a function of variations in measured calibration densities to expected densities.

2. The system of claim 1 wherein said calibrated media processing conditions are stored in said information member of said cassette.

3. A method for controlling image quality in processing radiographic photothermographic sheet media, comprising the steps of:

providing a thermal media processor for processing radiographic photothermographic sheet media, said media processor having a digital data memory and control system for storing digital data relating to processing conditions for at least one size of radiographic sheet media and for controlling said media processor;

providing packaging of unexposed radiographic photothermographic sheet media of said at least one size, said packaging having an information member storing relevant digital data including sheet media size and manufacturer's originated media processing conditions;

replacing any media processing conditions for said at least one size of radiographic sheet media stored in said processor digital data memory and control system with the manufacturer's originated media processing conditions stored on said packaging information member;

providing a calibration sheet media from said packaging of unexposed radiographic sheet media, said calibration sheet media having a plurality of different density regions;

processing said calibration sheet media by means of said media processor in accordance with the manufacturer's originated media processing conditions;

measuring the plurality of density regions of said processed calibration sheet media; and modifying said stored manufacturer's originated processing conditions for said at least one size of radiographic sheet media as a function of variations in measured calibration densities to expected densities, so as to store in said processor digital data memory and control system calibrated media processing conditions for use in processing subsequent sheet media from said packaging.

4. The method of claim 3 including placing the remaining unexposed radiographic sheet media from said packaging in a provided supply area for subsequent exposure and processing by said processor according to said calibrated media processing conditions.

* * * * *